United States Patent
Frenette et al.

(10) Patent No.: US 10,450,375 B2
(45) Date of Patent: Oct. 22, 2019

(54) METHODS OF TREATING SICKLE CELL DISEASE

(75) Inventors: Paul S. Frenette, New York, NY (US); Barry S. Coller, New York, NY (US); Aslihan Turhan, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 340 days.

(21) Appl. No.: 10/980,496

(22) Filed: Nov. 3, 2004

(65) Prior Publication Data
US 2005/0112124 A1    May 26, 2005

Related U.S. Application Data

(63) Continuation of application No. 10/123,373, filed on Apr. 15, 2002, now abandoned.

(60) Provisional application No. 60/283,776, filed on Apr. 13, 2001.

(51) Int. Cl.
*A61K 39/00* (2006.01)
*C07K 16/28* (2006.01)
*C07K 16/24* (2006.01)

(52) U.S. Cl.
CPC ........ *C07K 16/2839* (2013.01); *C07K 16/241* (2013.01); *C07K 16/2851* (2013.01); *A61K 2039/505* (2013.01)

(58) Field of Classification Search
None
See application file for complete search history.

(56) References Cited

U.S. PATENT DOCUMENTS 5,669,396 A * 9/1997 Golan et al. ............ 128/898
7,387,777 B2   6/2008 Wagner et al.

FOREIGN PATENT DOCUMENTS

WO   WO 98/13058   * 2/1998   ............ A61K 38/00
WO   WO 01/89564     11/2001

OTHER PUBLICATIONS

Buchanan et al., Hematology, 2004, p. 35-47, Review.*
Kutlar, Medical Princ Pract, 20205, 14, suppl 1: 15-19.*
Hebbel, The New England Journal of Medicine, 2000, 342: 1910-1912.*
Natarajan et al., Blood, 1996, 87: 4845-4952.*
Harlan, Blood, Jan. 2000, 95: 365-367.*
Belcher et al., Blood, 2000, 96: 2451-2459.*
Lonergan et al., RadioGraphics, 2001, 21:971-994.*
Erbe et al., J Cell Biol, 1992, 119: 215-227.*
Matsui et al. (2002). Heparin inhibits the flow adhesion of sickle red blood cells to P-selectin, Blood 100(10):3790-3796.
Turhan et al. (2002). Primary role for adherent leukocytes in sickle cell vascular occlusion: A new paradigm, Proc. Natl. Acad. Sci. U.S.A. 99(5):3047-3051.
Denis et al. (2001). Defect in regulated secretion of P-selectin affects leukocyte recruitment in von Willebrand factor-deficient mice. Proc Natl Acad Sci U S A. 98(7):4072-7.
Fabry et al (2001). Second generation knockout sickle mice: the effect of HbF, Blood 97,410-418.
Matsui et al (2001). P-selectin mediates the adhesion of sickle erythrocytes to the endothelium, Blood 98(6):1955-62.
Mclaney (2001). Novel cell mechanisms may lead to improved sickle cell treatment, UCSF Children's Hospital News, Sep. 6, 2001.
Trinkl (2001) UC Researchers have discovered novel cell adhesion mechanism that may lead to improved treatment for sickle cell disease. University of California, San Francisco Press Release, Sep. 6, 2001.
Wagener et al., (2001) Heme-induced cell adhesion in the pathogenesis of sickle-cell disease and inflammation. Trends Pharmacol Sci 22(2):52-4.
Belcher et al., (2000) Blood. Activated monocytes in sickle cell disease: potential role in the activation of vascular endothelium and vaso-occlusion. 96(7):2451-9.
Matsui et al. (2000). The novel adhesion of erythrocytes to P-selectln in sickle cell disease. Blood 96(11) Pt.1:600a.
Frenette et al (2000). P-Selectin glycoprotein ligand 1 (PSGL-I) is expressed on platelets and can mediate platelet-endothelial interactions In vivo, .J Exp Med 191, 1413-22.
Frenette et al (2000). Sulfated glycans-induce rapid hematopoietic progenitor cell mobilization: evidence for, selectin dependent and independent mechanisms. Blood 96, 2460-8.
Kaul et al. (2000). Hypoxia/reoxygenation causes Inflammatory response in transgenic sickle mice but not in normal mice [see comments], J Clin Invest 106,411-20.
Kaul et al. (2000). Monoclonal antibodies to alphaV beta3 (7E3 and LM609) inhibit sickle red blood cell-endothelium interactions induced by platelet-activating factor [see comments], Blood 95, 366-74.
Manodori et al. (2000). Adherence of phosphatidylserine-exposing erythrocytes to endothelial matrix Thrombospondin, Blood 95, 1293-300.
Terpstra et al. (2000). Scavenger receptors on liver Kupffer cells modulate the in vivo uptake of oxidatively damaged red blood cells in mice, Blood 95:2157-63.
Atweh et al (1999). Sustained induction of fetal haemoglobin by pulse butyrate therapy in sickle cell disease. Blood 93, 1790-7.
Closse et al. (1999). Phosphatidylserine-related adhesion of human erythrocytes to vascular endothelium, Br J. Haematol I07: 300-2.
Embury et al. (1999). In vivo blood flow abnormalities in the transgenic knockout sickle cell mouse, J Clin Invest 103:915-20.

(Continued)

*Primary Examiner* — Ileana Popa
(74) *Attorney, Agent, or Firm* — Marshall, Gerstein & Borun LLP

(57) ABSTRACT

The present invention relates to methods of treating sickle cell disease comprising reducing, in a subject in need of such treatment, the adherence between sickle RBCs and leukocytes. It is based, at least in part, on the discovery that leukocytes play a direct role in the initiation of venular occlusion. The present invention further provides for methods for identifying agents which decrease SS-RBC/leukocyte adherence and for animal models which may be used to further elucidate the mechanism of vaso-occlusion in sickle cell crises.

1 Claim, 9 Drawing Sheets

(56) References Cited

OTHER PUBLICATIONS

Hillery et al. (1999). The carboxy-terminal cell-binding domain of thrombospondin is essential for sickle red blood cell adhesion, Blood 94, 302-309.
Lard et al., (1999) Neutrophil activation in sickle cell disease.J Leukoc Biol. 1 66(3):411-5.
Ramos et al. (1999) Direct demonstration of P-selectin- and VCAM-1-dependent mononuclear cell rolling in early arthrosclerotic lesions of apolipoprotein E-deficient mice. Circ Res 84, 1237-44.
Robinson et al. (1999): Multiple targeted deficiencies in selectins reveal a predominant role, for, P-selectin in leukocyte recruitment, Proc Natl Acad Sci U S A 96, 1 1452-7.
Roszell et al. (1999). SAD sickle cell disease and fibrinogen deletion: negative interactive effects on, mouse survival and organ vasculopathy., Blood 94,198a.
Saleh et al. (1999). Levels of endothelial, neutrophil and platelet-specific factors•in sickle cell anemia patients during hydroxyurea therapy, Acta Haematol 102:31-7.
Vestweber et al. (1999). Mechanisms that regulate the function of the selectins and their ligands, Physiol Rev 79, 181-213.
Abboud et al (1998). Granulocylosis causing sickle-cell crisis [letter], Lancet 351, 959.
Faldon et al., (1998) Blood polymorphonuclear leukocytes from the majority of sickle cell patients in the crisis phase of the disease show enhanced adhesion to vascular endothelium and increased expression of CD64.Blood. 91(1):266-74.
Frenette et al. (1998). Platelet-endothelial interactions in inflamed mesenteric venules. Blood 91:1318-1324.
Jung et al (1998). Gene-targeted mice reveal importance of L-selectin-dependent rolling ' for neutrophil adhesion, Am J Physiol 274:1785-91.
Mazo et al. (1998); Hematopoietic progenitor cell rolling in bone marrow microvessels: parallel contributions by endothelial selectins and vascular cel! adhesion, molecule 1, J. Exp Med 188,465-74.
Nagel (1998). A knockout of a transgenic mouse—animal models of sickle cell anemia, N Engl J Med 339, 194-5.
Schwartz et al. (1998) Two distinct pathways mediate the formation of intermediate density cells and hyperdense cells from normal density sickle red blood cells, Blood 92:4844-55.
Udani et al. (1998). Basal.cell adhesion molecule Lutheran protein. The receptor critical for sickle cell adhesion to laminin, J Clin Invest 101, 2550-8.
Borgstrom et al. (1997). Leukocyte adhesion in angiogenic blood vessels. Role of E-selectin, P-selectin, and beta2 integrin in lymphotoxin-mediated leukocyte recruitment, in tumor microvessels, J Clin Invest 99: 2246-53.
Frenettte et al. (1997). Insights into selectin function from knockout mice. Thromb Haemost 78:60-64.
Paszty et al. (1997). Transgenic knockout mice with exclusively human sickle hemoglobin and sickle cell disease, Science 278:876-8.
Ramos et al. (1997), Differential effect of P-selectin antibodies on neutrophil rolling and recruitment to inflammatory sites, Blood 89,3009-18.
Ryan et al. (1997). Knockout-transgenic mouse model of sickle cell disease Science 278:873-6.
Thevenin et al. (1997). Band 3 peptides block the adherence of sickle .cells lo endothelial cells in vitro, Blood 90,417-419.
Xie et al. (1997). In vivo rolling and endothelial selectin binding of mononuclear leukocytes is distinct from that of polymorphonuclear cells, Eur J Immunol 27:2935-41.
Bullard et al. (1996). Infectious susceptibility and severe deficiency of leukocyte rolling and recruitment in E-selectin and P-selectin double mutant mice., J Exp Med 183,2329-2336.
Frenette et al (1996). Endothelial selectins and vascular cell adhesion, molecule-1 promote hematopoietic progenitor homing lo bone marrow. Proc Natl Acad Sci USA 95, 14423-8.
Frenette et al. (1996). Adhesion molecules—Part II: Blood vessels and blood cells., N Eng J Med 335,43-45.
Frenette et al. (1996). Susceptibility to Infection and altered hematopoiesis in mice deficient in both P- and E-selectins., Cell 84, 563574.
Hofstra et al (1996), Sickle erythrocytes adhere to polymorphonuclear neutrophils and. activate the neutrophil respiratory burst, Blood 87: 4440-7.
Joneckis et al. (1996). Glycoprotein IV-independent adhesion of sickle red blood cells to immobilized thrombospondin under flow conditions, Blood 87:4862-70.
Kansas, G. S. (1996). Selectins and their ligands: current concepts and controversies. Blood 88:3259-3287.
Kasschau et al. (1996). Adhesion of sickle neutrophils and erythrocytes to fibronectin, Blood 87: 771-80.
Kumar et al. (1996). Phorbol ester stimulation increases sickle erythrocyte adherence to endothelium: a novel pathway involving alpha 4 beta 1 integrin receptors on sickle reticulocytes and fibronectin, Blood 88, 4348-58.
Schweitzer et al. (1996). Constitutive expression of E-selectin and vascular cell adhesion molecule on endothelial cells of hematopoietic tissues. Am J Pathol 148, 165-175.
Subramaniam et al. (1996). Defects in hemolysis in P-selectin-deficient mice. Blood 87:1238-1242.
Wood et al. (1996). Increased erythrocyte phosphatidylserine exposure in sickle cell disease: flow-cytometric measurement and clinical associations, Blood 88:1873-80.
Frenette et al. (1995). Platelets roll on stimulated endothelium In vivo: An interaction mediated by endothelial P-selectin Proc Natl Acad USA 92,7450-7454.
Gee et al. (1995). Sickle reticulocytes adhere to VCAM-1, Blood 85:268-74.
Ley et al. (1995). Sequential contribution of L- and P-selectin 16 leukocyte rolling in vivo. J Exp Med 181, 669-675.
Trudel et al. (1994). Sickle cell disease of transgenic SAD mice, Blood 84:3189-97.
Brittain et al (1993). Thrombospondin from activated platelets promotes sickle erythrocyte adherence to human microvascular endothelium under physiologic flow; a potential role for platelet activation in sickle cell vaso-occlusion. Blood 81:2137-43.
Joneckis et al. (1993) Integrin alpha 4 beta 1 and glycoprotein IV (CD36) are expressed on circulating reticulocytes in sickle cell anemia, Blood 82:3548-55.
Kaul et al. (1993). Sickle erythrocyte endothelial interactions in microcirculation: the role of .von Willebrand factor and implications for vaso-occlusion, Blood 81, 2429-38.
Swerlick et al. (1993). Alpha 4 beta 1-integrin expression on sickle reticulocytes: vascular cell adhesion molecule-d-dependent binding, to endothelium, Blood 82, 1891-9.
Sugihara et al. (1992). Thrombospondin mediates adherence of CD36+ sickle reticulocytes to endothelial cells, Blood 80, 2634-42.
Trudel et al. (1991). Towards a transgenic mouse model of sickle cell disease: hemoglobin SAD, EMBO J 10, 3157-66.
Kaul et al. (1989). Microvascular sites and characteristics of sickle cell adhesion to vascular endothelium in shear flow conditions: pathophysiological implications, Proc Natl Acad Sci USA 86, 3356-60.
Lipowsky et al., (1989). Role of leukocyte-endothelium adhesion in affecting recovery from ischemic episodes. Ann NY Acad Sci 565:308-15.
Barabino et al. (1987). Rheological studies of erythrocyte-endothelial cell interactions in sickle cell disease, Prog Clin Biol Res 240, 113-27.
Wick et al. (1987). Unusually large von Willebrand factor multimers increase adhesion of sickle erythrocytes to human endothelial cells under controlled flow, J Clin Invest 80,905-10.
Mohandas et al. (1985). Sickle erythrocyte adherence to vascular endothelium. Morphologic correlates and the requirement for divalent cations and collagen-binding plasma proteins, J Clin Invest 76:1605-12.
Hebbel et al., (1985) The adhesive sickle erythrocyte: cause and consequence of abnormal interactions with endothelium, monocytes/macrophages and model membraries. Clin Haematol 14(1):141-61.
Wautier et al., (1983) Factors involved in cell adhesion to vascular endothelium. Blood Cells 9(2):221-34.

(56) References Cited

OTHER PUBLICATIONS

Hebbel et al (1980). Abnormal adherence of sickle erythrocytes to cultured vascular endothelium: possible mechanism for, microvascular occlusion in sickle cell disease, J Clin Invest 65, 154-60.

Hebbel et al. (1980). Erythrocyte adherence to endothelium in sickle-cell anemia. A possible determinant of disease severity, N Engl J Med 302, 992-5.

Hoover et al. (1979). Adhesion of normal and sickle erythrocytes to endothelial monolayer cultures. Blood 54:872-6.

Boggs et al (1973). An unusual pattern of neutrophil kinetics in sickle cell anemia, Blood 41, 59-65.

Revelle et al., 1996, "Structure-Function Analysis of P-selectin-Sialyl Lewis$^X$ Binding Interactions," J. Biol. Chem. 271:4289-4297.

Bänteli et al., 2000, "Potent E-selectin antagonists," Helvetica Chemica Acta 83:2893-2907.

Simanek et al., 1998, "Selectin-Carbohydrate Interactions: From Natural Ligands to Designed Mimics," Chem. Rev. 98:833-862.

Dupré et al., 1996, "Glycomimetic Selectin Inhibitors: (α-D-mannopyranosyloxy)methylbiphenyls," Bioorganic & Med Chemistry Letts 6(5):569-572.

Sprengard et al., 1996, Synthesis and Biological Activity of Novel Sialyl-Lewis$^X$ Conjugates, Bioorganic & Med Chemistry Letts 6(5):509-514.

Mulligan et al., 1993, "Protective effects of oligosaccharides in P-selectin-dependent lung injury," Nature 364:149-151

Handa et al., 1991, "Selectin GMP-140 (CD62;PADGEM) Binds to Sialosyl-Le$^X$ and Sialosyl-Le$^X$, and Sulfated Glycans Modulate This Binding," Biochem. Biophys. Res. Commun. 181(3):1223-1230.

Charache et al., Effect of hydroxyurea on the frequency of painful crises in sickle cell anemia. *N. Engl. J. Med.*, 332(2): 1317-22 (1995).

Griffin et al., High-dose intravenous methylprednisolone therapy for pain in children and adolescents with sickle cell disease. *N. Engl. J. Med.* 330(11): 733-7 (1994).

Hidalgo et al., Heterotypic interactions enabled by polarized neutrophil microdomains mediate thromboinflammatory injury. *Nat. Med.*, 15(4): 384-91 (2009).

Labow et al., Characterization of E-selectin-deficient mice: Demonstration of overlapping function of the endothelial selectins. *Immunity*, 1: 709-20 (1994).

Lee et la., Sickle cell adhesion to laminin: Potential role for the α5 chain. *Blood*, 92: 2951-8 (1998).

Parsons et al., Lutheran blood group glycoprotein and its newly characterized mouse homologue specifically bind α5 chain-containing human laminin with high affinity. *Blood*, 97: 312-20 (2001).

Schwartz et al., Increased adherence of sickled and phosphatidylserine-enriched human erythrocytes to cultured human peripheral blood monocytes. *J. Clin. Invest.* 75: 1965-72 (1985).

\* cited by examiner

METHODS OF TREATING SICKLE CELL DISEASE

This application is a continuation of U.S. patent application Ser. No. 10/123,373 filed Apr. 15, 2002 now abandoned, which claims priority to Provisional U.S. Patent Application No. 60/283,776 filed Apr. 13, 2001, incorporated by reference in their entireties herein.

This invention was made with government support under Grant Nos. HL28381, DK56638 and HL19278 awarded by the National Institutes of Health. The government has certain rights in the invention.

INTRODUCTION

The present invention relates to methods for treating sickle cell disease in which adherence between sickled erythrocytes and leukocytes is inhibited. It is based, at least in part, on the discovery that, in animal models of sickle cell disease, sickled erythrocyte/leukocyte adhesion plays a direct role in the initiation of vaso-occlusion, the cause for sickle cell crises in humans.

BACKGROUND OF THE INVENTION

Half a century ago, Linus Pauling first showed that sickle cell anemia is a molecular disease (Pauling, 1949; for full citations see list in Section 8, infra). It was later demonstrated that the disease originated from a missense mutation within the β-globin gene, leading to the substitution of valine for glutamic acid on the outer surface of the globin molecule. This amino acid substitution renders the sickle cell hemoglobin ("HbS") less soluble and prone to polymerization upon deoxygenation (Hoffman, 2000). Erythrocytes (red blood cells, "RBC") carrying polymerized HbS are thus less deformable and may obstruct microvessels. This vascular occlusion, producing tissue ischemia and infarction, represents a major cause of morbidity and mortality among sickle cell disease patients. Despite recent therapeutic advances with the use of hydroxyurea and butyrate (Charache, 1995; Atweh, 1999) many patients remain severely symptomatic and thus, may benefit from alternate therapeutic modalities.

Over the years, it has become clear that the clinical manifestations of sickle cell disease extend far beyond the homozygous globin mutation. Seminal findings were the discovery that sickle ("SS") RBCs, unlike normal RBCs, could adhere to stimulated endothelium in vitro and that SS-RBCs' adhesion correlated with the clinical severity of sickle cell disease(Hoover, 1979; Hebbel, 1980 (a) and (b)). Subsequent studies have recognized the importance of plasma factors in SS-RBC adhesion to the endothelium (Wautier, 1983; Mohandas, 1984) and revealed that the deformable "low-density" cells were more adherent than the dense sickle-shaped cells (Mohandas, 1985; Barbarino, ). Other elegant studies by Kaul and coworkers subsequently showed using a rat mesocecum ex vivo perfusion model that SS-RBCs adhered exclusively in venules (mostly small post-capillary and collecting venules) and confirmed that adhesion was density-class dependent (light-density reticulocytes and young discocytes being most adherent; Kaul, 1989). Collectively, these observations lead to the current multistep model, shown in FIG. 1A, by which light-density SS-RBCs first adhere in post-capillary venules, after which secondary trapping of dense cells may produce vascular obstruction and local ischemia. These transient obstructions may induce HbS polymerization, which would increase RBC rigidity and exacerbate vascular occlusion.

Multiple adhesion molecules have been shown to participate in SS-RBC/endothelium interactions (FIG. 1B), Soluble adhesion molecules and matrix proteins were first recognized, and may function as a bridge between two cellular adhesion receptors or may recruit SS-RBCs directly to the vessel wall's matrix. These include fibrinogen and fibronectin (Wautier, 1983; Kasschau, 1996), von Willebrand factor (vWF; Wick, 1987; Kaul, 1993), laminin (Hillery, 1996; Lee, 1998) and thrombospondin ("TSP;Sugihara, 1992; Hillery, 1999). Several putative cellular counter-receptors have been suggested, although many are controversial or still poorly defined. For example, studies have suggested that TSP may interact with integrin associated protein (CD47; Gao, 1996) and sulfated glycolipids (Hillery, 1996), phosphatidylserine (Mandori, 2000) and CD36 (Sugihara, 1992) on the SS-RBC membrane. Other studies have suggested that CD36 is not involved in TSP-mediated sickle cell adhesion (Hillery, 1996; Joneckis, 1996). Membrane damage to SS-RBC with loss of phospholipid asymmetry (Frank, 1985) may expose phosphatidylserine as well as sulfated glycolipids which can interact with vWF and laminin (Roberts, 1986). Membrane damage to SS-RBC might also expose a portion of band 3 which may contribute to SS-RBC's adhesion with endothelial cells (Thevenin, 1997). Basal cell adhesion molecule/Lutheran protein (B-CAM-LU), the protein that carries the Lutheran blood group, was also shown to be a laminin receptor in SS-RBCs (Udani, 1998; Parsons, 2001). Finally, the integrin $\alpha_4\beta_1$, one of the first sickle RBC adhesion receptor identified on sickle reticulocytes (Swerlick, 1993; Joneckis, 1993; Gee, 1995), can interact with vascular cell adhesion molecule-1 ("VCAM-1") on activated endothelium. To date, few receptors for SS-RBCs have been identified on activated endothelium. In addition to VCAM-1 (Swerlick, 1993; Gee, 1995), $\alpha_5\beta_3$ has been proposed to play an important role since functional inhibition of this receptor drastically reduced SS-RBC accumulation on platelet activating factor ("PAF")-stimulated microvasculature in the ex vivo rat mesocecum (Kaul, 2000). Recent data also indicate that P-selectin may mediate SS-RBC adhesion to endothelial cells (Matsui, 2000). The foregoing studies of SS-RBC adhesion, however, suffer the shortcoming of having been performed in vitro or, in the case of Kaul, 2000, ex vivo; the mechanisms of vaso-occlusion had not, prior to the present invention, been explored in vivo.

Several mouse strains expressing HbS have been generated in the last decade. These transgenic strains have been used to study the pathophysiology of sickle cell disease in vivo, and may be divided into two broad categories: i) transgenic mice expressing both the endogenous murine and human globin genes, and (ii) transgenic mice expressing exclusively human globin genes (Nagel, 1998). So-called "SAD" mice represent one example of transgenic animal models for sickle cell disease in which the human β-globin transgene contains three natural mutations that enhance Hb sickling: HbS, HbS-Antilles and Hb D Punjab (hence the acronym "SAD"). RBCs from SAD mice carry approximately 19% human hemoglobin. Although associated with a significant perinatal mortality (when a SAD mouse is bred with a wild-type animal, the frequency of SAD offspring is about 30%, rather than the expected 50%), adult SAD transgenic mice are relatively healthy, suffering neither anemia nor reticulocytosis unless exposed to hypoxemic conditions (Trudel, 1991; Trudel, 1994). Transgenic "knock-outs" (hereinafter referred to as "sickle cell" or "SS" mice)

were developed by sequential breeding of mice deficient in α and β globins with transgenic animals expressing both human a and β$^s$ globins; such SS mice are genetically identified as Tg(Hu-miniLCRα1$^G$γ$^4$γδβ$^S$)mα−/−β−/−. These animals display a drastic phenotype characterized by severe anemia with high reticulocyte counts, splenomegaly and evidence of end-organ damage (Paszty, 1997; Ryan, 1997). Although the hematological and histological pictures in SS mice resemble that of patients, the phenotype in mice is more severe and their viability is reduced. When a male SS mouse is bred with a mouse heterozygous for β-globin expression (Tg(Hu-miniLCRα1$^G$γ$^4$γδβ$^S$)mα−/−β−/+), less than 10% of the offspring exclusively express human globins, instead of the expected 50%. The reduced viability of SS mice has hampered the progression of in vivo studies and the development of useful models to evaluate the mechanisms of vaso-occlusion.

It had been noted, prior to the present invention, that sickle cell patients with leukocyte counts greater than 15,000/microliter have an increased risk of death (Platt, 1994), that lower neutrophil counts were associated with a lower crises rate in sickle cell patients treated with hydroxyurea (Churache, 1996) and that treatment with granulocyte colony stimulating factor ("G-CSF", which increases leukocyte counts) induced a sickle cell crisis (Abboud, 1998). Schwartz, 1985, reported increased adherence of sickle RBCs to cultured peripheral blood monocytes in vitro, wherein irreversibly sickled RBCs and deoxygenated RBCs were most adherent and adhesion appeared to correlate with the exposure of phosphatidylserine to the outer membrane leaflet. Hofstra et al., 1996, reported that, in vitro, SS-RBCs can bind activated neutrophils in a static in vivo adhesion assay, an interaction which was more pronounced in the presence of autologous sickle cell plasma. Binding of SS-RBCs to activated neutrophils was partially inhibited by RGDS peptides and human IgG, suggesting than one or more integrin(s) and neutrophil Fc receptors may be involved. SS-RBC adhesion also induced an oxidative burst characterized by the production of free radicals by activated neutrophils (Id.) Further, it had been noted that anti-inflammatory agents such as methylprednisolone may be effective in decreasing the duration of sickle cell crisis episodes (Griffin, 1994). A recent study using a sickle cell mouse model indicated that the inflammatory response (number of adherent and emigrated leukocytes and oxidant production) resulting from hypoxia and reoxygenation was increased in sickle cell transgenic mice compared to control animals (Kaul, 2000).

Prior to the present invention, however, it had not been appreciated which of the many potential aspects of the inflammatory response was directly associated with vaso-occlusion.

SUMMARY OF THE INVENTION

The present invention relates to methods of treating sickle cell disease comprising reducing, in a subject in need of such treatment, the adherence between sickled RBCs and leukocytes. It is based, at least in part, on the discovery that leukocytes play a direct role in the initiation of venular occlusion. The present invention further provides for methods for identifying agents which decrease SS-RBC/leukocyte adherence and for animal models which may be used to further elucidate the mechanism of vaso-occlusion in sickle cell crises.

DETAILED DESCRIPTION OF THE INVENTION

Figure 1B:
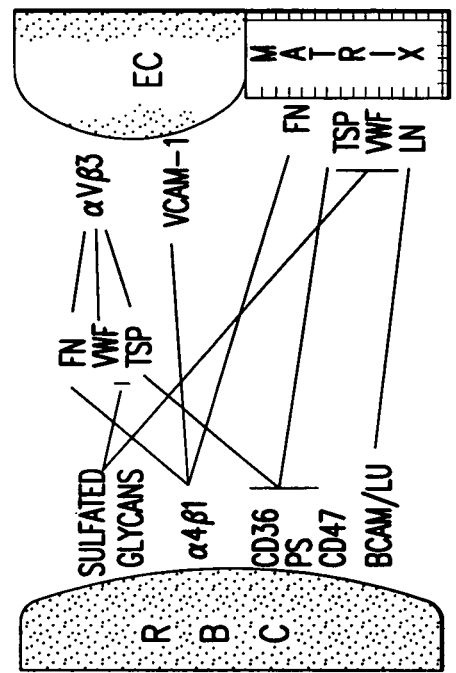
FIGS. 1A-B. Erythrocyte interactions with the vessel wall. (A) depicts the current paradigm's conception of events leading to vaso-occlusion. (B) depicts putative adhesion pathways involved in the interactions of RBCs, endothelial cells ("ECs") and the vascular matrix. PS=phosphatidylserine; BCAM/Lu=basal cell adhesion molecules/Lutheran protein; FN=fibronectin; vWF=von Willebrand factor; TSP=thrombospondin; LN=laminin; VCAM-1=vascular cell adhesion molecule-1.
Figure 1A:
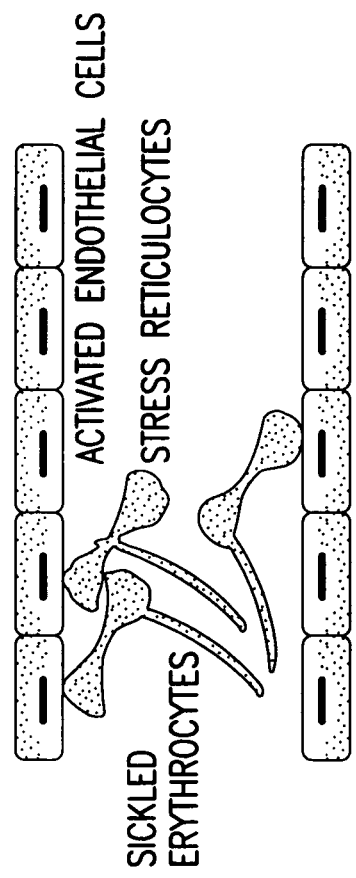

For clarity of disclosure, and not by way of limitation, the detailed description of the invention is divided into the following subsections:

(a) methods of treating sickle cell disease;
(b) methods of identifying agents useful in treating sickle cell disease; and
(c) animal model systems.

Methods of Treating Sickle Cell Disease

The present invention provides for methods of treating sickle cell disease in which venular occlusion by sickle erythrocytes ("SS-RBCs", which contain HbS and may be in the sickled or in a discoid conformation) adherent to leukocytes is decreased. The phrase "method of treating" sickle cell disease is used herein to indicate decreasing the occurrence and/or severity of any one or more of the following signs and symptoms: pain, anemia, infection, stroke, tissue damage, visual impairment, bone infarction, jaundice, and gall stones, and the manifestations of "sickle cell crisis".

The methods of the present invention may intervene in the process by which SS-RBC adhere to leukocytes and initiate venular occlusion at the point where a SS-RBC adheres to a leukocyte and/or the point at which a leukocyte and/or the SS-RBC/leukocyte complex binds to the venule endothelium. Such methods may be directed at the cellular level (for example, decreasing the number of leukocytes) or may be directed at the molecular interactions between the SS-RBC and leukocyte or between the leukocyte or the SS-RBC/leukocyte complex and the endothelial cell.

The recruitment of leukocytes into inflamed tissue has been well characterized at the molecular level. It is now recognized that leukocyte extravasation represents a multi-step process initiated by leukocyte tethering and rolling along the vessel wall of post-capillary venules. The tethering and rolling steps are largely mediated by selectins and their ligands. Rolling on selectins and their ligands allows leukocytes to interact with chemokines on the surface of the activated endothelium. These chemokines may activate the leukocyte and change the conformation of $\beta_2$ integrins into a high-affinity state, allowing firm adhesion and subsequent diapedesis via the interactions of integrins and immunoglobulin superfamily members (reviewed in Springer, 1995; Frenette, 1996; Vestweber, 1999). The selectin family consists of three members containing a functional calcium-binding lectin domain. Two selectins are expressed by endothelial cells (P- and E-selectins) and one is found on most leukocytes (L-selectin) (Kansas, 1996). Genetic analyses using knockout experiments have shown distinct functions for each selectin (Frenette, 1997; Robinson et al., 1999). While mice lacking a single selectin gene have mildly aberrant phenotypes, animals deficient in both endothelial selectins (P/E−/−) show virtually no leukocyte rolling even after cytokine-induced (tumor necrosis factor alpha; "TNF-α") inflammation (Frenette et al., 1996; Bullard et al., 1996). The profound defect in leukocyte adhesion and extravasation in P/E−/− mice, reminiscent of mice lacking all $\beta_2$ integrins, such as mice which are CD18−/− (Wilson et al., 1993; Scharffetter-Kochanek et al., 1998) suggested that overlapping function of the two endothelial selectins is as important for leukocyte adhesion in vivo as are $\beta_2$ integrins. In addition to four $\beta_2$ integrins ($\alpha_L\beta_2$(LFA-1), $\alpha_M\beta_2$ (Mac-1), $\alpha_X\beta_2$ and $\alpha_D\beta_2$) leukocytes express other integrins such as $\alpha_V\beta_3$ and $\beta_1$ (on lymphocytes and monocytes but not neutrophils; Carlos, 1994).

Accordingly, the present invention provides for methods of decreasing vaso-occlusion associated with sickle cell disease by inhibiting SS-RBC/leukocyte/endothelial adhesion along any one or several steps in the adhesion process.

Such methods may, for example, but not by way of limitation, inhibit the binding between leukocytes and endothelial P- and/or E-selectin or the binding of leukocyte L-selectin to the endothelium. Such binding may be inhibited, for example, using an immunoglobulin specific for a selectin molecule, such as a P-, E-, and/or L-selectin molecule, or a fragment or derivative of such immunoglobulin. Alternatively, such binding may be inhibited using a non-inmunoglobulin molecule which interacts with the calcium-binding lectin domain of the selectin molecule, including molecules which interfere with calcium binding to the site.

In other non-limiting embodiments, vaso-occlusion in a sickle cell patient may be decreased by inhibiting the interaction of leukocytes or RBC/leukocyte complexes with cytokines on the surface of activated endothelium. As a non-limiting specific example, an agent which inhibits TNF-α, such as an anti-TNF immunoglobulin, fragment or derivative thereof, may be administered.

In further non-limiting embodiments, vaso-occlusion in a sickle cell patient may be decreased by inhibiting the binding between one or more elements selected from the group consisting of leukocytes, SS-RBC/leukocyte complexes, and endothelial cells, via a $\beta_2$ integrin molecule. Thus, binding (i) among leukocytes, or (ii) among SS-RBC/leukocyte complexes, or (iii) between a SS-RBC/leukocyte complex and a leukocyte, or (iv) between an endothelial cell and a SS-RBC/leukocyte complex, or (v) between an endothelial cell and a leukocyte, may be inhibited, for example, by an agent which interferes with binding of a $\beta_2$ integrin molecule, where a $\beta_2$ integrin molecule participates, directly or indirectly, in the binding between partners. For example, a leukocyte may be bound to another leukocyte indirectly by binding to an endothelial cell, and an endothelial cell may be bound to another endothelial cell indirectly via a plurality of adherent SS-RBC/leukocyte complexes.

In specific non-limiting examples, binding to $\alpha_L\beta_2$(LFA-1), $\alpha_M\beta_2$ (Mac-1), $\alpha_X\beta_2$, and/or $\alpha_D\beta_2$ may be inhibited. Such inhibition may be achieved, for example, using an immunoglobulin molecule, or a fragment or derivative thereof, which specifically binds to the integrin.

In related embodiments, vaso-occlusion in a sickle cell patient may be decreased by inhibiting the change in the conformation of $\beta_2$ integrins into a high-affinity state. Such inhibition may be effected by an immunoglobulin molecule, fragment or derivative thereof or by a small non-immunoglobulin molecule.

In additional non-limiting embodiments, vaso-occlusion in a sickle cell patient may be decreased by inhibiting binding among or between elements selected from the group consisting of an endothelial cell, a platelet, a leukocyte, and a SS-RBC/leukocyte complex by inhibiting binding via a $\beta_3$ integrin, for example, $\alpha_{IIb}\beta_3$ or $\alpha_V\beta_3$ integrin. By inhibiting binding via a $\beta_3$ integrin, binding between an endothelial cell and either a leukocyte, or a SS-RBC/leukocyte complex, or a platelet, or a SS-RBC/leukocyte/platelet complex, or a platelet/SS-RBC complex, may be inhibited. Such inhibition may be achieved, for example, using an immunoglobulin molecule or a fragment or derivative thereof which binds to a $\beta_3$ integrin. Non-limiting examples of antibodies which bind to $\alpha_V\beta_3$ integrin include the murine monoclonal antibody 7E3 (deposited with the American Type Culture Collection at ATCC HB 8832), the humanized chimeric equivalent of 7E3, c7E3, the Fab fragment of c7E3 (which is sold commercially as ReoPro®), and the monoclonal antibody LM609 and chimeric equivalents. 7E3, c7E3, and Fab 7E3 also bind to $\alpha_{IIb}\beta_3$. Where c7E3 or ReoPro is used, the dosage may be, in specific non-limiting embodiments, between 0.1-0.3 mg/kg, and preferably 0.25 mg/kg. Preferably, after 0.25 mg/kg is administered, the patient may further receive intravenous infusion of 0.125 m/kg/min for a therapeutically effective period of time.

In further non-limiting embodiments, vaso-occlusion in a sickle cell patient may be decreased by inhibiting binding between one or more elements selected from the group consisting of leukocytes, SS-RBC/leukocyte complexes, and endothehal cells, via $\beta_1$ integrins. Such inhibition may be achieved using an immunoglobulin molecule, or a fragment or derivative thereof, which specifically binds to the $\beta_1$ integrin.

In further non-limiting embodiments, vaso-occlusion in a sickle cell patient may be decreased by inhibiting the binding of leukocytes or SS-RBC/leukocyte complexes to von Willebrand factor (vWf). Such inhibition may be achieved using an immunoglobulin molecule, or a fragment or derivative thereof, which specifically binds to the vWf In further non-limiting embodiments, vaso-occlusion in a sickle cell patient may be decreased by inhibiting the binding of leukocytes or SS-RBC/leukocyte complexes to thrombospondin. Such inhibition may be achieved using an immunoglobulin molecule, or a fragment or derivative thereof, which specifically binds to the thrombospondin.

In further non-limiting embodiments, vaso-occlusion in a sickle cell patient may be decreased by inhibiting the binding of leukocytes or RBC/leukocyte complexes to a molecule, such as, but not limited to, ICAM-1, VCAM-1, or their ligands CD18 and $\alpha_4\beta_1$. Such inhibition may be achieved using an immunoglobulin molecule, or a fragment or derivative thereof, which specifically binds to the endothelial adhesion molecule.

Methods of Identifying Agents Useful in Treating Sickle Cell Disease

The present invention provides for methods of identifying agents useful in treating sickle cell disease which comprise determining whether a test agent is able to modulate the adhesion of SS-RBC to leukocytes and thereby to venular endothelium. Such methods may be practiced in vitro or in vivo. Examples of in vitro studies may include assays which test for SS-RBC/leukocyte binding by, for example, co-precipitation or co-sedimentation, or by retention on a solid matrix.

Alternatively, the effectiveness of the test agent at inhibiting adhesion may be evaluated in vivo. For example, but not by way of limitation, the test agent may be evaluated using intravital microscopy, using techniques as set forth in Example Section 6 below.

The ability of a test agent to inhibit the binding of a SS-RBC to a leukocyte, and/or inhibit the binding of a SS-RBC/leukocyte complex or a leukocyte to an endothelium or to endothelial cells, indicates that the test agent may be useful in the treatment of sickle cell disease. In certain although not all circumstances, it may be desirable to determine that the test agent selectively blocks adhesion of sickled rather than non-sickled erythrocytes; in such circumstances, the amount of available oxygen may be decreased or increased to maximize or minimize, respectively, the formation of SS-RBC.

Because many of the molecules involved in the adhesion pathway are important to normal biological function, it may be desirable to select for agents which have a short half life for administration during sickle cell crises, or which change conformation and become more active at lower oxygen tensions.

Animal Model Systems

The present invention further provides for animal model systems which are designed to lack one or more element of the adhesion pathway, including, for example, those elements set forth in Section 5.1, supra. Such animals may be transgenic animals, including, but not limited to, transgenic mice, lacking or, alternatively, overexpressing a gene encoding a protein selected from the group consisting of a selectin, such as P-, E- or L-selectin; a chemokine, such as TNF-α; a $\beta_2$ integrin, such as $\alpha_L\beta_2$(LFA-1), $\alpha_M\beta_2$ (Mac-1), $\alpha_X\beta_2$, and $\alpha_D\beta_2$; a $\beta_3$ integrin, for example, $\alpha_V\beta_3$; a $\beta_1$ integrin; vWf, thrombospondin, ICAM-1, VCAM-1, CD18 and $\alpha_4\beta_1$.

EXAMPLE

Sickle Cell Interactions with Adherent Leukocytes can Initiate Venular Occlusion in Sickle Cell Mice Materials and Methods. Sickle cell breeding pairs were obtained from Dr. Mohandas Narla at the Lawrence Berkeley Institute, and were maintained according to Dr. Narla's instructions. "Heterozygotes", referred to herein as "SA" mice, express the sickle transgene, are deficient in a globin and heterozygous for the β-globin locus, and are genetically Tg(Hu-miniLCRα1$^G\gamma^4\gamma\delta\beta^S$)mα−/−β−/+. Female SA mice were bred with male sickle cell mice, which express exclusively human globins, and are genetically Tg(Hu-miniLCRα1$^G\gamma^4\gamma\delta\beta^S$)mα−/−β−/−. After the progeny from these breedings were weaned, a drop of blood was obtained from a tail biopsy to permit phenotyping by hemoglobin electrophoresis. To generate large numbers of male sickle cell mice, a bone marrow transplantation strategy was used which aimed at reconstituting the entire blood compartment of several recipient mice from precursors obtained from a single sickle cell mouse. Fresh femoral bone marrow cells were obtained from one female sickle cell and one "heterozygous" control mouse (derived from the same genetic background as the sickle animals; Paszty, 1997). Wild-type male C57B1/6 recipient mice were lethally irradiated with 1200cGy, in two split doses, and injected, under a sterile hood, with bone marrow nucleated cells from SS or SA animals, at a dose of $1.5\times10^6$ cells per recipient. Following the procedure, transplanted animals were transferred into a sterile cage containing sterile food and water (see Frenette, 1998, Frenette, 2000). Since the life-span of the normal mouse RBC is approximately 55 days (Hoffman-Fezer, 1993), mice were allowed to recover for at least two months prior to evaluation for engraftment and chimerism.

Figure 2:
FIG. 2. Triton-X-100 gel electrophoresis of tail blood samples; 10 micrograms of protein, determined spectrophotometrically, were loaded per lane. The first two lanes represent normal mouse and human hemoglobin and the next five lanes represent mixtures with decreasing amounts of human hemoglobin.

Between 8 and 12 weeks after transplantation, blood was obtained from a small tail incision and hemoglobin was separated on a polyacrylamide gel containing urea and Triton-X-100 (Alter et al., 1980); the results are shown in FIG. 2. 10 micrograms of protein, determined spectrophotometrically, were loaded per lane. The first two lanes represent normal mouse and human hemoglobin and the next five lanes represent mixtures with decreasing amounts of human hemoglobin. Under these electrophoretic conditions, the mouse and human β globins co-migrate; however, the mouse and human α globin can be easily distinguished. The various hemoglobin mixtures demonstrate that the assay can detect as little as 1-2% human hemoglobin. The second half of the gel are samples from representative animals transplanted with SS bone marrow, and shows that the RBCs from four wild-type ("WT") recipients and three P−/E− −/− mice (see Section 7, infra) contained >97% human globins. In addition, wild-type animals transplanted with SS bone marrow cells (hereafter referred to as SS-WT) were severely anemic and displayed very significant splenomegaly, compared with animals that received SA bone marrow (SA-WT). Thus, these results indicate that the SS phenotype can be transplanted into adult wild-type recipient mice.

The cremasteric microcirculation of the highly chimeric animals was evaluated using intravital microscopy. The surgical preparation of the cremaster muscle itself induces inflammatory stimuli leading to leukocyte rolling and progressive recruitment of adherent leukocytes. More severe inflammation may be induced by administering TNF-α, an inflammatory cytokine which induces P- and E-selectin-mediated leukocyte rolling (Frenette, 1996; Bullard, 1996). Because inflammation is clinically known to trigger sickle cell crises, chimeric mice were treated with murine recombinant TNF-α (0.5 micrograms intrascrotally) 3.5 hours prior to preparing the cremaster muscle for intravital microscopy (Frenette, 1996; Frenette, 1998; Ley, 1995; Bullard, 1996). While treatment with TNF-α was tolerated well in SA-WT controls, SS-WT mice died during or soon after surgery. However, 55 transplants survived the surgery when not pre-treated with the cytokine or when treated with a half dose of TNF-α (however, the half-dose did not produce meaningful inflammation, as assessed by the lack of leukocyte rolling velocities). The following protocol was therefore designed to induce a progressive inflammatory response in SS and SA transplants (FIG. 3).

Figure 3:
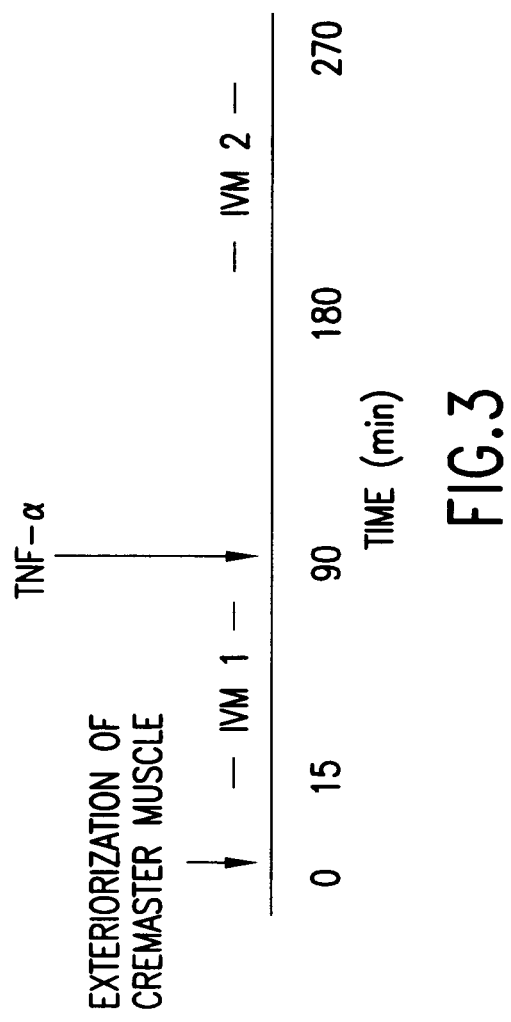
FIG. 3. Diagrammatic representation of intravital microscopy ("IVM") protocol. The two recording periods are designated IVM-1 and IVM-2.

As depicted diagrammatically in FIG. 3, mice were prepared for the cremasteric intravital microscopy using standard procedures (Pemberton, 1993; Kaul, personal communication). Mice were anesthetized with urethane/chlorose and a tracheostomy was made to facilitate spontaneous respiration. Immediately after the cremaster dissection, the animal was placed on a plexiglass stage and the cremaster muscle was continuously perfused with an endotoxin-free bicarbonated solution (NaCl 135 mM, KCl 5 mM, $NaHCO_3$ 27 mM, $MgCl_2$ 0.64 mM) equilibrated with 95% $N_2$/5% $CO_2$ at 37° C. The tissue was allowed to stabilize for 15 minutes, at which point microvessels (post-capillary and collecting venules) were videotaped until 90 minutes after surgery IVM-1; FIG. 3). At the 90 minute time point, TNF-α (0.5 micrograms, intraperitoneally) was injected and allowed to take effect for 90 minutes, and microvessels were recorded for 90 minutes IVM-2; FIG. 3). When possible, approximately 7-10 venules were recorded before and after TNF-α administration in each experiment. Prior to timing each vessel, centerline RBC velocities were measured in real time using an optical doppler velocimeter. Vessel diameter and shear rates were determined as previously described (Frenette, 1996).

Results and Conclusions. Vaso-occlusion is a major cause of morbidity and mortality in sickle cell disease. To better understand the pathophysiology of vaso-occlusion in vivo, intravital microscopy was performed in (1) C57B1/6 wild-type ("WT") mice; (2) mice exclusively expressing sickle cell hemoglobin ("SS"; [Tg(Hu-miniLCRα1$^G$γ$^4$γδβ$^S$) mα-/-β-/-]); and (3) lethally irradiated WT mice transplanted with bone marrow from either SS mice or mice heterozygous for sickle hemoglobin ("SA";human β$^S$/mouse β[Tg(Hu-miniLCRα1$^G$γ$^4$65 δβ$^S$)mα-/-β-/+].

In the transplant recipients, three months after transplantation, SS bone marrow recipients had >96% donor hemoglobin and displayed severe anemia (hematocrit 21±3%; n=10, p<0.05), high reticulocyte counts and splenomegaly, by comparison, heterozygous bone marrow recipients had nearly normal hematocrits (32±3%; n=7) and only a slight increase in spleen weight (ratio: 5±1).

The cremasteric muscle of the mice was then surgically dissected, and "small" (15-20 μm) and "large" (30-50 μm) venules were visualized between 15-90 minutes after surgery and after treatment with Tumor Necrosis Factor cc ("TNF-α"; 0.5 μg/mouse). The surgery itself produced an inflammatory response leading to leukocyte adhesion, and this response was accentuated by TNF-α treatment.

Figure 4A:
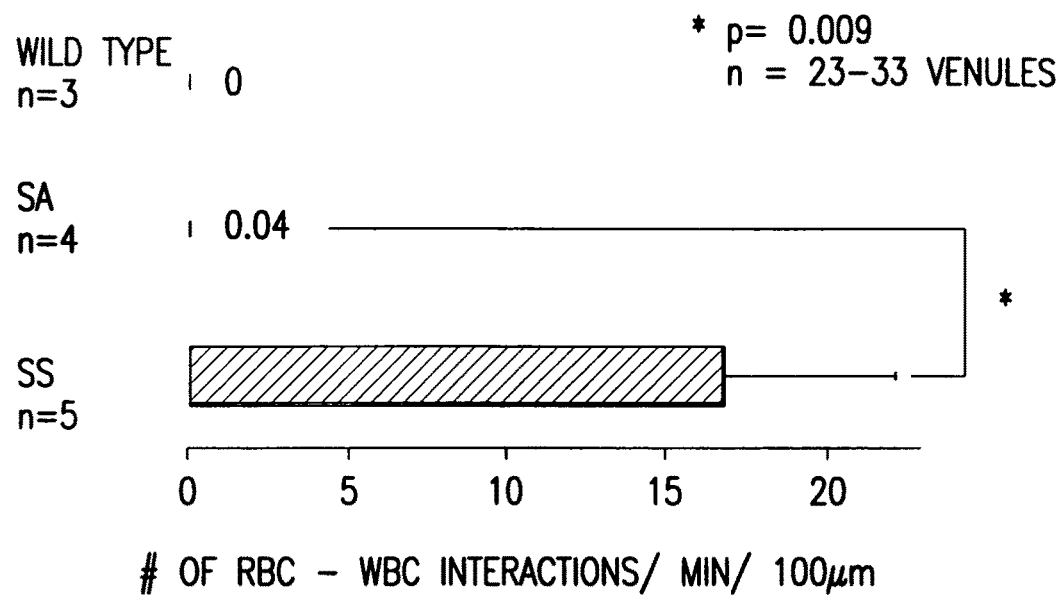
FIGS. 4A-B. Erythrocyte/leukocyte interactions in wild-type, SA and SS-transplanted mice in vivo. (A) depicts the number of RBC/leukocyte interactions quantitated in venules filmed between 30 and 90 minutes after cremaster surgery, expressed as the number of interactions per minute per 100 microns of venular length. (B) shows that the number of RBC/leukocyte interactions correlates with time after surgery. Each dot in the scattergraph represents a single venule.
Figure 4B:
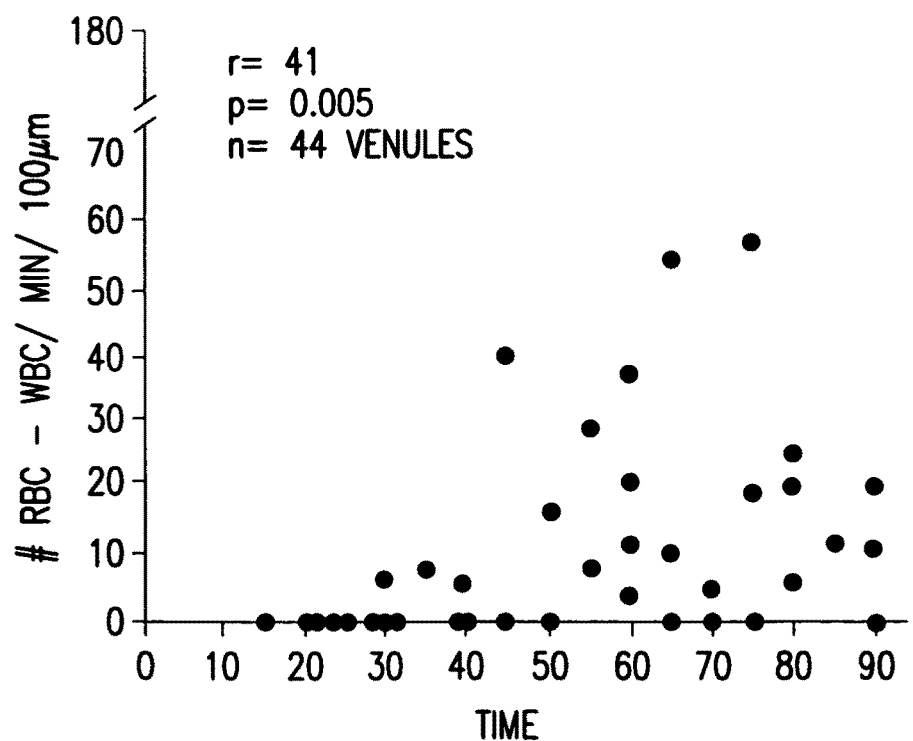

Although occasionally direct interaction between SS-RBCs and the vasculature was observed, the most striking finding was that numerous SS-RBCs interacted with adherent leukocytes in venules activated by surgery alone and these interactions were increased after TNF α administration. On average, 17±5 SS-RBCs interacted with adherent leukocytes per minute over 100 μm venular length in SS-BMT mice (n=34 venules in 5 mice) (FIG. 4A). These interactions began approximately 30 minutes after the surgery and continued throughout the observation period (FIG. 4B). Similar interactions were seen in non-transplanted SS mice. Very few SS-RBC/leukocyte interactions were observed in SA-BMT animals (0.04±0.03/min/100 μm; n=24 venules in 4 mice) and none were seen in wild-type animals. The graph in FIG. 4B shows that there were relatively few RBC/leukocyte interactions in the first half of the IVM-1 period, and that the number of interactions drastically increased during the second half of filming (r=0.41, p=0.005).The tethers resisted the shear stress of the flowing blood and lasted up to 100 seconds. In small venules, SS-RBCs formed transient bridges between adherent leukocytes and between adherent leukocytes and the endothelium, resulting in obstruction of blood flow which could be either transient or prolonged. Following TNF-α stimulation, continuous SS-RBC/leukocyte adhesion events lead to a significant decrease in blood flow in SS-BMT mice compared to SA-BMT animals (shear rates: 501±35 versus 110±29; n=30-32; p<0.0001).

Figure 5C:
FIGS. 5A-C. Digital stillframes obtained from intravital microscopy of the cremaster microcirculation stimulated by TNF-α. (A) is an image from an inflamed venule (30 microns) from an SA-transplanted animal showing adherent (white arrows) and rolling (white stars) leukocytes; no RBC are seen since free-flowing RBC move too rapidly to be distinguished by this technique. Blood flow is from right to left. (B) is an image from an inflamed venule (20 microns) from an SS-transplanted mouse showing numerous RBCs (arrowheads) interacting with adherent leukocytes (arrows). Blood flow is left to right. (C) is an image from a large venule with two adherent leukocytes in the center (arrows). One leukocyte has "captured" two RBCs (one sickle-shaped (arrowhead), the other discoid). Diagonal bars mark the vessel wall. Blood flow is from bottom to top.
Figure 5B:
Figure 5A:

FIGS. 5A-C illustrate examples of digital still frames obtained from representative video recordings. FIG. 5A shows a venule stimulated by surgery followed by TNF-α treatment. Rolling and adherent leukocytes are present but RBC adhesive interactions are rare (none were seen in this mouse). In FIG. 5B, numerous SS-RBCs (elongated cells, white arrowheads) are seen to interact with adherent leukocytes (arrows). Consistent with a true adhesive interaction (as compared to physical trapping), RBC/leukocyte interactions can resist the shear of venules for several seconds. This is particularly evident in FIG. 5C, an image taken of a large venule (approx. 90 microns) where two SS-RBCs, one sickled in shape (arrowhead) the other with a normal discoid shape, remained bound to an adherent leukocyte, resisting the shear of flowing blood. Although most interacting RBCs appear to be sickle-shaped, normal discoid cells were occasionally seen, as in FIG. 5C. This suggests that, unlike sickle/endothelium adhesion, the cell density profile may not play an important role in the interaction with adherent leukocytes (or the high-density cells may be more adherent to leukocytes). It should also be noted that in small venules (<20 microns), the interaction of few RBCs (or only one RBC in the smallest venule) with one adherent leukocyte could transiently (or permanently) occlude blood flow.

Figure 6:
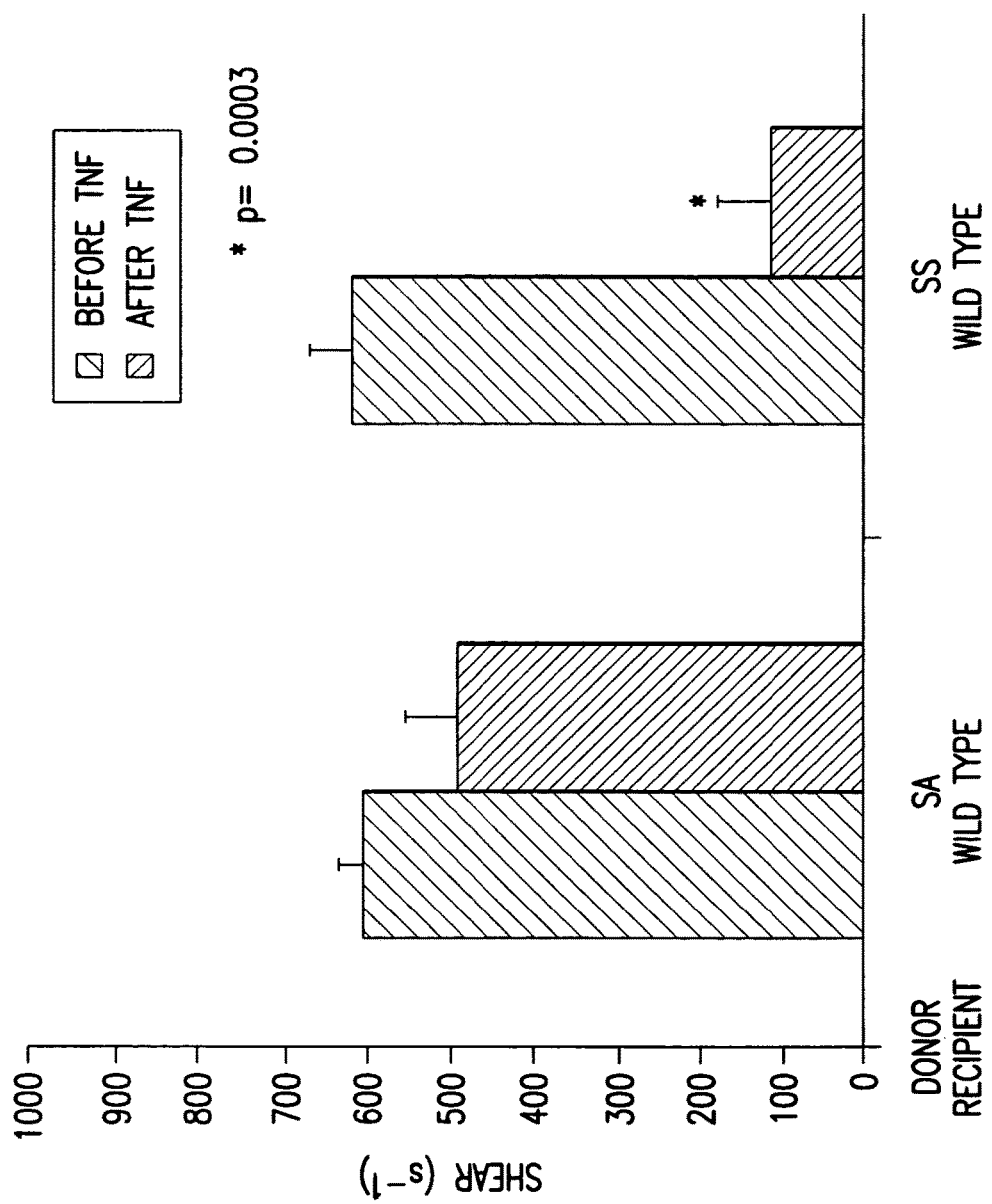
FIG. 6. Shear rates in cremasteric venules before and after TNF-α administration.

After TNF-α, RBC/leukocyte interactions increased (or persisted) in SS-WT mice (but were not increased in SA-WT animals) and lead to a progressive reduction in blood flow in the cremaster microvasculature. FIG. 6 illustrates the shear rates before and after TNF-α administration in SA and SS transplants. Shear rates are directly proportional to the mean RBC velocity and inversely proportional to the vessel diameter. While shear rates between SA and SS transplants were similar before TNF-α, shear rates were significantly reduced after TNF-α in SS mice (approximately 80 percent reduction) compared to SA mice. Moreover, four out of the five studied SS transplanted mice died during the recording after TNF-α administration whereas there was no lethality in the SA-WT group. Since TNF-α increases the number of adherent leukocytes in venules (Morita, 1995; Ley, 1995), these results suggest that TNF-α administration to SS transplanted mice leads to a severe (often lethal) vaso-occlusive crisis. However, it was also possible that TNF-α might produce other lethal effects in SS-WT mice that are independent of leukocyte adhesion.

These observations suggest a critical role for SS-RBC/leukocyte interactions in initiating vaso-occlusive episodes in sickle cell mice. They are in accord with the documented correlation between low leukocyte counts and reduced painful crises in hydroxyurea-treated patients as well as in in vitro studies of SS-RBC/leukocyte interactions by Hofstra et al.

EXAMPLE

Figure 7A:
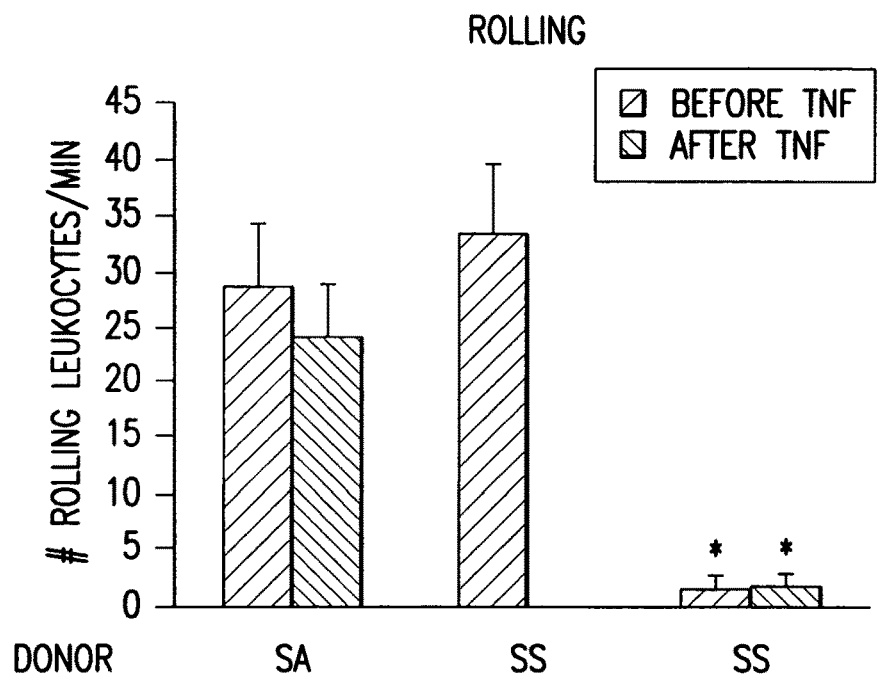
FIGS. 7A-B. Leukocyte rolling and adhesion in cremasteric venules. The numbers of rolling (A) and adherent (B) leukocytes were determined on video recordings from intravital microscopy experiments. n=30-44 venules from 3-5 mice; *p<0.0005, #p<0.005.
Figure 7B:
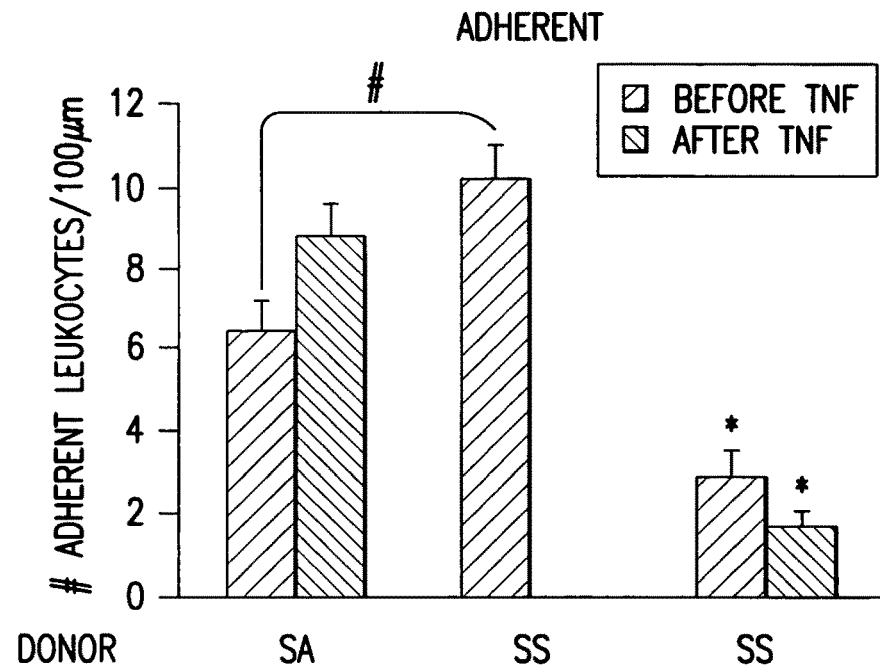
Figure 8A:
FIG. 8A-B. P- and E-selectin deficiency protects from vaso-occlusion. (A) is a view of two post-capillary venules (arrows) and a collecting venule from a SS-P/E−/− transplanted mouse after TNF-α stimulation. No leukocyte rolling and very little leukocyte adhesion were observed and the blood flow (left to right) was preserved. (B) depicts shear rates before and after TNF-α administration in SS-P/E−/− transplanted mice. The wild-type recipients, shown in FIG. 6, are shown for comparison.
Figure 8B:
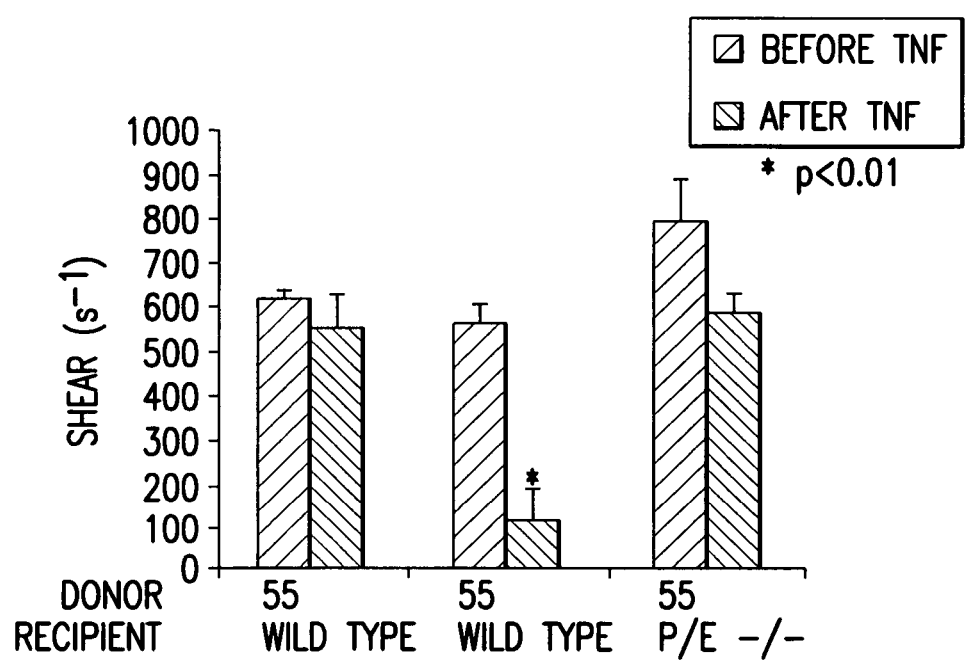

P- and E-Selection Deficiency Protects Against TNF-α Induced Vascular Occlusion in Sickle Mice: Evidence for a Critical Role for Adherent Leukocytes To further evaluate the role of adherent leukocytes in sickle cell disease, bone marrow from mice exclusively expressing sickle cell hemoglobin ("SS";[Tg(Hu-miniLCRα1$^G\gamma^S\gamma\delta\beta^S$)mα-/-β-/-]) was transplanted into mice lacking both P- and E-selectins (P/E-/-). P/E-/- mice have severe defects in leukocyte rolling and adhesion in inflamed venules. Experimental data (FIGS. 7A-B) indicates that the amount of leukocyte rolling and adhesion and the blood flow was preserved even after TNF-α stimulation (shear rates: 604±57, n=29) (FIGS. 8A-B). The interactions per adherent leukocyte were not, however, altered.

Consistent with reduced numbers of adherent leukocytes in SS-P/E -/- mice, the total number of erythrocyte/leukocyte interactions was significantly reduced in P/E-/- mice harboring SS-RBCs (0.4±0.3/min/100 μm; n=23 in 3 mice; p=0.01). It is interesting to note that the remaining adherent leukocytes present in endothelial selectin-deficient venules could still interact with SS-RBCs, suggesting that P/E selectins are not necessary for SS-RBC/leukocyte interactions.

Unlike SS-WT mice which for the most part died during the intravital experiment, all SS-P/E-/- mice survived the entire experiment. These results strongly support a role for adherent leukocytes in initiating vasoconstriction by interacting with circulating sickle erythrocytes, and indicate that P- and E-selectin deficiencies protect SS mice from vaso-occlusion. Moreover, the data suggest that the absolute number of interacting leukocytes in a given venule, rather than the rate of interactions per leukocyte, appear to be a critical factor in venular occlusion.

Determination of blood counts and assessment of spleen weight/body weight ratios among various transplanted and non-transplanted groups revealed several abnormalities. The preliminary blood counts were done after TNF-α treatment, except 4 SS bone marrow donor mice (Table 1, 4th row), which were performed at baseline conditions. In addition to being severely anemic, these resting SS mice exhibited severe leukocytosis, in contrast to WT or SA mice which showed a mild leukocytosis after TNF-α (normal WT WBC counts are ~3 to 5×10$^3$/μl). WBCs were lower after TNF-α administration in SS mice, possibly resulting from increased adhesion to the vessel wall during inflammation. Both SS-WT and SA-WT chimeras displayed blood counts similar to their non-transplanted donor counterparts, suggesting that this transplantation model reproduced very well the phenotype of sickle cell mice.

Leukocytosis was also more severe in P/E-/- mice expressing SS hemoglobin. Interestingly, the blood from TNF-α treated SS mice (and from the chimeras generated by transplantation) contained much fewer platelets suggesting platelet consumption during the vaso-occlusive process. Although this might suggest a role for platelets in vaso-occlusion, the fact that a similar reduction in platelet numbers is seen in SS⇒P/E-/- mice (and that SS⇒P/E-/- mice are protected) argues that platelets may not be necessary for vaso-occlusion. The lower spleen weight in transplanted mice compared to their non-transplanted controls likely results from the fact that transplanted animals have had sickle cell disease for only a few weeks.

8. Citations

Abboud, M., Laver, J., and Blau, C. A. (1998). Granulocytosis causing sickle-cell crisis [letter], Lancet 351, 959.

Alter, B. P., and Goff, S. C. (1980). A murine model for the switch from fetal to adult hemoglobin during ontogeny, Blood 56, 1100-5.

Alter, B. P., Goff, S. C., Efremov, G. D., Gravely, M. E., and Huisman, T. H. (1980). Globin chain electrophoresis: a new approach to the determination of the G gamma/A gamma ratio in fetal haemoglobin and to studies of globin synthesis, Br J Haematol 44, 527-34.

Anderson, D. C., and Springer, T. A. (1987). Leukocyte adhesion deficiency: an inherited defect in the Mac 1, LFA-1 and p150.95 glycoproteins., Annu Rev Med 38, 175-194.

Atweh, G. F., Sutton, M., Nassif, I., Boosalis, V., Dover, G. J., Wallenstein, S., Wright, E., McMahon, L., Stamatoyannopoulos, G., Faller, D. V., and Perrine, S. P. (1999). Sustained induction of fetal hemoglobin by pulse butyrate therapy in sickle cell disease [see comments], Blood 93, 1790-7.

Barabino, G. A., McIntire, L. V., Eskin, S. G., Sears, D. A., and Udden, M. (1987). Rheological studies of erythrocyte-endothelial cell interactions in sickle cell disease, Prog Clin Biol Res 240, 113-27.

Berkow, R. L., Wang, D., Larrick, J. W., Dodson, R. W., and Howard, T. H. (1987). Enhancement of neutrophil superoxide production by preincubation with recombinant human tumor necrosis factor, J Immunol 139, 3783-91.

Boas, F: E., Forman, L., and Beutler, E. (1998). Phosphatidylserine exposure and red cell viability in red cell aging and in hemolytic anemia, Proc Natl Acad Sci USA 95, 3077-81.

TABLE 1

Blood counts and spleen weights of intact and transplanted mice

| | TNF-α | Leukocytes ×10$^3$/μl | Hematocrit (%) | Platelets (×10$^6$/μl) | Spleen wgt. ratio (g/g BW × 10$^{-3}$) |
|---|---|---|---|---|---|
| WT (n = 3) | Yes | 7.0 ± 1.3 | 43.9 ± 6.9 | 1009 ± 326 | 3.0 ± 0.4 |
| SA mice (n = 6) | Yes | 10.7 ± 2.4 | 29.8 ± 5.6 | 1500 ± 162 | 5.0 ± 0.3 |
| SA ⇒ WT (n = 4) | Yes | 6.3 ± 0.3 | 35.1 ± 0.6 | 1008 ± 32 | 3.0 ± 0.1 |
| SS mice (n = 4) | No | 46.1 ± 9.1 | 19.7 ± 1.5 | 636 ± 108 | N/E |
| SS mice (n = 4) | Yes | 14.3 ± 5.3 | 12.6 ± 2.5 | 288 ± 52 | 53 ± 1 |
| SS ⇒ WT (n = 4) | Yes | 23.0 ± 2.9 | 11.2 ± 0.6 | 272 ± 19 | 28 ± 2 |
| SS ⇒ P/E-/- (n = 3) | Yes | 84.7 ± 14.9 | 21.7 ± 5.1 | 233 ± 62 | 39 ± 5 |

Blood was harvested by retroorbital venous sampling after cremasteric surgery and TNF-α administration (3-4 hrs after 0.5 ug TNF-α) or upon baseline conditions ("no" TNF-α), and blood counts were determined using a Coulter counter.
The arrow (⇒) indicates bone marrow transplantation.
Wgt, weight; BW, body weight; N/E, not evaluated.

Boggs, D. R., Hyde, F., and Srodes, C. (1973). An unusual pattern of neutrophil kinetics in sickle cell anemia, Blood 41, 59-65.

Borgstrom, P., Hughes, G. K., Hansell, P., Wolitsky, B. A., and Sriramarao, P. (1997). Leukocyte adhesion in angiogenic blood vessels. Role of E-selectin, P-selectin, and beta2 integrin in lymphotoxin-mediated leukocyte recruitment in tumor microvessels, J Clin Invest 99, 2246-53.

Bornstein, P. (1992). Thrombospondins: structure and regulation of expression, Faseb J 6, 3290-9.

Bornstein, P., Devarayalu, S., Li, P., Disteche, C. M., and Framson, P. (1991). A second thrombospondin gene in the mouse is similar in organization to thrombospondin 1 but does not respond to serum, Proc Natl Acad Sci USA 88, 8636-40.

Bowen, J. D., Petersdorf, S. H., Richards, T. L., Maravilia, K. R., Dale, D. C., Price, T. H., St John, T. P., and Yu, A. S. (1998). Phase I study of a humanized anti-CD11/CD18 monoclonal antibody in multiple sclerosis, Clin Pharmacol Ther 64, 339-46.

Bowie, E. J., Solberg, L. A., Fass, D. N., Johnson, C. M., Knutson, G. J., Stewart, M. L., and Zoecklein, L. J. (1986). Transplantation of normal bone marrow into a pig with severe von Willebrand's disease, J Clin Invest 78, 26-30.

Brittain, H. A., Eckman, J. R., Swerlick, R. A., Howard, R. J., and Wick, T. M. (1993). Thrombospondin from activated platelets promotes sickle erythrocyte adherence to human microvascular endothelium under physiologic flow; a potential role for platelet activation in sickle cell vaso-occlusion, Blood 81, 2137-43.

Bullard, D. C., Kunkel, E. J., Kubo, H., Hicks, M. J., Lorenzo, I., Doyle, N. A., Doerschuk, C. M., Ley, K., and Beaudet, A. L. (1996). Infectious susceptibility and severe deficiency of leukocyte rolling and recruitment in E-selectin and P-selectin double mutant mice., J Exp Med 183, 2329-2336.

Carlos, T. M., and Harlan, J. M. (1994). Leukocyte-endothelial adhesion molecules, Blood 84, 2068-2101.

Charache, S., Barton, F. B., Moore, R. D., Terrin, M. L., Steinberg, M. H., Dover, G. J., Ballas, S. K., McMahon, R. P., Castro, O., and Orringer, E. P. (1996). Hydroxyurea and sickle cell anemia. Clinical utility of a myelosuppressive "switching" agent. The Multicenter Study of Hydroxyurea in Sickle Cell Anemia, Medicine (Baltimore) 75, 300-26.

Charache, S., Terrin, M. L, Moore, R. D., Dover, G. J., Barton, F. B., Eckert, S. V., McMahon, R. P., and Bonds, D. R. (1995). Effect of hydroxyurea on the frequency of painful crises in sickle cell anemia. Investigators of the Multicenter Study of Hydroxyurea in Sickle Cell Anemia [see comments], N Engl J Med 332, 1317-22.

Closse, C., Dachary-Prigent, J., and Boisseau, M. R. (1999). Phosphatidylserine-related adhesion of human erythrocytes to vascular endothelium, Br J Haematol 107, 300-2.

Condliffe, A. M., Chilvers, E. R., Haslelt, C., and Dransfield, I. (1996). Priming differentially regulates neutrophil adhesion molecule expression/function, Immunology 89, 105-11.

Denis, C., Methia, N., Frenette, P. S., Rayburn, H., Ullman-Cullere, M., Hynes, R. O., and Wagner, D. D. (1998). A mouse model of severe von willebrand disease: defects in hemostasis and thrombosis, Proc Natl Acad Sci USA 95, 9524-9529.

Denis, C. V., Andre, P., Saffaripour, S., and Wagner, D. D. (2001). Defect in regulated secretion of P-selectin affects leukocyte recruitment in von Willebrand factor-deficient mice., Proc Natl Acad Sci. USA in press.

Devitt, A., Moffatt, O. D., Raykundalia, C., Capra, J. D., Simmons, D. L., and Gregory, C. D. (1998). Human CD14 mediates recognition and phagocytosis of apoptotic cells, Nature 392, 505-9.

Embury, S. H., Mohandas, N., Paszty, C., Cooper, P., and Cheung, A. T. (1999). In vivo blood flow abnormalities in the transgenic knockout sickle cell mouse, J Clin Invest 103, 915-20.

Fabry, M. E., Suzuka, S. M., Weinberg, R. S., Lawrence, C., Factor, S. M., Gilman, J. G., Costantini, F., and Nagel, R. L. (2001). Second generation knockout sickle mice: the effect of HbF, Blood 97, 410418.

Fadok, V. A., Bratton, D. L., Rose, D. M., Pearson, A., Ezekewitz, R. A., and Henson, P. M. (2000). A receptor for phosphatidylserine-specific clearance of apoptotic cells, Nature 405, 85-90.

Francis, R. B., and Haywood, L. J. (1992). Elevated immunoreactive tumor necrosis factor and interleukin-1 in sickle cell disease, J Natl Med Assoc 84, 611-5.

Franck, P. F., Bevers, E. M., Lubin, B. H., Comfurius, P., Chiu, D. T., Op den Kamp, J. A., Zwaal, R. F., van Deenen, L. L., and Roelofsen, B. (1985). Uncoupling of the membrane skeleton from the lipid bilayer. The cause of accelerated phospholipid flip-flop leading to an enhanced procoagulant activity of sickled cells, J Clin Invest 75, 183-90.

Frenette, P. S., Denis, C. V., Weiss, L., Jurk, K., Subbarao, S., Kehrel, B., Hartwig, J. H., Vesiweber, D., and Wagner, D. D. (2000). P-Selectin glycoprotein ligand 1 (PSGL-1) is expressed on platelets and can mediate platelet-endothelial interactions in vivo, J Exp Med 191, 1413-22.

Frenette, P. S., Johnson, R. C., Hynes, R. O., and Wagner, D. D. (1995). Platelets roll on stimulated endothelium in vivo: An interaction mediated by endothelial P-selectin.; Proc Natl Acad USA 92, 7450-7454.

Frenette, P. S., Mayadas, T. N., H., R., Hynes, R. O., and Wagner, D. D. (1996). Susceptibility to infection and altered hematopoiesis in mice deficient in both P-and E-selectins., Cell 64, 563-574.

Frenette, P. S., Moyna, C., Hartwell, D. W., Lowe, J. B., Hynes, R. O., and Wagner, D. D. (1998a). Platelet-endothelial interactions in inflamed mesenteric venules., Blood 91,1318-1324.

Frenette, P. S., Subbarao, S., Mazo, I. B., von Andrian, U. H., and Wagner, D. D. (1998b). Endothelial selectins and vascular cell adhesion molecule-1 promote hematopoietic progenitor homing to bone marrow., Proc Natl Acad Sci USA 95, 14423-8.

Frenette, P. S., and Wagner, D. D. (1996). Adhesion molecules-PartII: Blood vessels and blood cells., N Eng J Med 335, 43-45.

Frenette, P. S., and Wagner, D. D. (1997). Insights into selectin function from knockout mice., Thromb Haemost 78, 60-64.

Frenette, P. S., and Weiss, L. (2000). Sulfated glycans induce rapid hematopoietic progenitor cell mobilization: evidence for selectin-dependent and independent mechanisms [In Process Citation], Blood 96, 2460-8.

Gamble, J. R., Harlan, J. M., Klebanoff, S. J., and Vadas, M. A. (1985). Stimulation of the adherence of neutrophils to umbilical vein endothelium by human recombinant tumor necrosis factor, Proc Natl Acad Sci USA 82, 8667-71.

Gao, A. G., Lindberg, F. P., Finn, M. B., Blystone, S. D., Brown, E. J., and Frazier, W. A. (1996). Integrin-associated protein is a receptor for the C-terminal domain of thrombospondin, J Biol Chem 271, 21-4.

Gee, B. E., and Platt, O. S. (1995). Sickle reticulocytes adhere to VCAM-1, Blood 85, 268-74.

Gerszten, R. E., Lim, Y. C., Ding, H. T., Snapp, K., Kansas, G., Dichek, D. A., Cabanas, C., Sanchez-Madrid, F., Gimbrone, M. A., Rosenzweig, A., and Luscinskas, F. W. (1998). Adhesion of monocytes to vascular cell adhesion molecule-1-transduced human endothelial cells: implications for atherogenesis, Circ Res 82, 871-8.

Ginis, I., and Faller, D. V. (1997). Protection from apoptosis in human neutrophils is determined by the surface of adhesion, Am J Physiol 272, C295-309.

Ginis, I., Zaner, K., Wang, J. S., Paviotsky, N., and Tauber, A. I. (1992). Comparison of actin changes and calcium metabolism in plastic- and fibronectin-adherent human neutrophils, J Immunol 149, 1388-94.

Griffin, T. C., McIntire, D., and Buchanan, G. R. (1994). High-dose intravenous methylprednisolone therapy for pain in children and adolescents with sickle cell disease [see comments], N Engl J Med 330, 733-7.

Hahne, M., Jager, U., Isenmann, S., Hallmann, R., and Vestweber, D. (1993). Five tumor necrosis factor-inducible cell adhesion mechanisms on the surface of mouse endothelloma cells mediate the binding of leukocytes, J Cell Biol:121, 655-64.

Harlow, E. and Lane, D. (1988). Antibodies: A laboratory manual (Colds Spring Harbor, N.Y., Colds Spring Harbor Laboratory Press).

Haug, C. E., Colvin, R. B., Delmonico, F. L., Auchincloss, H., Tolkoff-Rubin, N., Preffer, F. I., Rothlein, R., Norris, S., Scharschmidt, L., and Cosimi, A. B. (1993). A phase I trial of immunosuppression with anti-ICAM-1 (CD54) mAb in renal allograft recipients, Transplantation 55, 766-72; discussion 772-3.

Hebbel, R. P., Boogaerts, M. A., Eaton, J. W., and Steinberg, M. H. (1980a). Erythrocyte adherence to endothelium in sickle-cell anemia. A possible determinant of disease severity, N Engl J Med 302, 992-5.

Hebbel, R. P., Yamada, O., Moldow, C. F., Jacob,. H. S., White, J. G., and Eaton, J. W. (1980b). Abnormal adherence of sickle erythrocytes to cultured vascular endothelium: possible mechanism for microvascular occlusion in sickle cell disease, J Clin Invest 65, 154-60.

Hendey, B., Lawson, M., Marcantonio, E. E., and Maxfield, F. R. (1996). Intracellular calcium and calcineurin regulate neutrophil motility on vitronectin through a receptor identified by antibodies to integrins alphav and beta3, Blood 87, 2038-48.

Hidalgo, A., Weiss, L. A., and Frenette, P. S. (2000). Intravital microscopy in NOD/SCID mice reveals defects in human cord blood CD34+ cell rolling and adhesion in bone marrow microvessels., Blood 96, 580a.

Hillery, C. A., Du, M. C., Montgomery, R. R., and Scott, J. P. (1996). Increased adhesion of erythrocytes to components of the extracellular matrix: isolation and characterization of a red blood cell lipid that binds thrombospondin and laminin, Blood 87, 4879-86.

Hillery, C. A., Scott, J. P., and Du, M. C. (1999). The carboxy-terminal cell-binding domain of thrombospondin is essential for sickle red blood cell adhesion, Blood 94, 302-9.

Hodivala-Dilke, K. M., McHugh, K. P., Tsakiris, D. A., Rayburn, H., Crowley, D, Ullman-Culler, M., Ross, F. P., Coller, B. S., Teitelbaum, S., and Hynes, R. O. (1999). beta3-integrin-deficient mice are a model for Glanzmann thrombasthenia showing placental defects and reduced survival, J Clin Invest 103, 229-238.

Hoffman, R. (2000). Hematology: basic principles and practice, 3rd edn (New York, Churchill-Livingstone).

Hoffmann-Fezer, G., Mysliwietz, J., Mortlbauer, W., Zeitler, H. J., Eberle, E., Honle, U., and Thierfelder, S. (1993). Biotin labeling as an alternative nonradioactive approach to determination of red cell survival, Ann Hematol 67, 81-7.

Hofstra, T. C., Kalra, V. K., Melselman, H. J., and Coates, T. D. (1996), Sickle erythrocytes adhere to polymorphonuclear neutrophils and activate the neutrophil respiratory burst, Blood 87, 4440-7.

Hoover, R., Rubin, R., Wise, G., and Warren, R. (1979). Adhesion of normal and sickle erythrocytes to endothelial monolayer cultures, Blood 54, 872-6.

Huang, S., Endo, R. I., and Nemerow, G. R. (1995). Upregulatlion of integrins alpha v beta 3 and alpha v beta 5 on human monocytes and T lymphocytes facilitates adenovirus-mediated gene delivery, J Virol 69, 2257-63.

Hynes, R. O. (1992). Integrins: versatility, modulation, and signaling in cell adhesion, Cell 69, 11-25.

Joneckis, C. C., Ackley, R. L., Orringer, E. P., Wayner, E. A., and Parise, L. V. (1993). Integrin alpha 4 beta 1 and glycoprotein IV (CD36) are expressed on circulating reticulocytes in sickle cell anemia, Blood 82, 3548-55.

Joneckis, C. C., Shock, D. D., Cunningham, M. L., Orringer, E. P., and Parise, L. V. (1996). Glycoprotein IV-independent adhesion of sickle red blood cells to immobilized thrombospondin under flow conditions, Blood 87, 4862-70.

Jung, U., Ramos, C. L., Bullard, D. C., and Cey, K. (1998). Gene-targeted mice reveal importance of L-selectin-dependent rolling for neutrophil adhesion, Am J Physiol 274, H1785-91.

Kansas, G. S. (1996). Selectins and their ligands: current concepts and controversies., Blood 88, 3259-32.87.

Kasschau, M. R., Barabino, G. A., Bridges, K. R., and Golan, D. E. (1996). Adhesion of sickle neutrophils and erythrocytes to fibronectin, Blood 87, 771-80.

Kaul, D. K., Fabry, M. E., and Nagel, R. L. (1989). Microvascular sites and characteristics of sickle cell adhesion to vascular endothelium in shear flow conditions: pathophysiological implications., Proc Natl Acad Sci USA 86, 3356-60.

Kaul, D. K., and Hebbel, R. P. (2000). Hypoxia/reoxygenation causes inflammatory response in transgenic sickle mice but not in normal mice [see comments], J Clin Invest 106, 411-20.

Kaul, D. K., Nagel, R. L., Chen, D., and Tsai, H. M. (1993) Sickle erythrocyte-endothelial interactions in microcirculation: the role of von Willebrand factor and implications for vasoocclusion, Blood 81, 2429-38.

Kaul, D. K., Tsai, H. M., Liu, X. D., Nakada, M. T., Nagel, R. L., and Coller, B. S. (2000). Monoclonal antibodies to alphaVbeta3 (7E3 and LM609) inhibit sickle red blood cell-endothelium interactions induced by platelet-activating factor [see comments], Blood 95, 368-74.

Kettritz, R., Xu, Y. X., Kerren, T., Quass, P., Klein, J. B., Luft, F. C., and Haller, H. (1999). Extracellular matrix regulates apoptosis in human neutrophils, Kidney Int 55, 562-71.

Kishimoto, T. K., Jutila, M. A., Berg, E. L., and Butcher, E. C. (1989). Neutrophil Mac-1 and MEL-14 adhesion proteins inversely regulated by chemotactic factors., Science 245, 1238-1241.

Kumar, A., Eckmam, J. R., Swerlick, R. A., and Wick, T. M. (1996). Phorbol ester stimulation increases sickle erythrocyte adherence to endothelium: a novel pathway involving alpha 4 beta 1 integrin receptors on sickle reticulocytes and fibroectin, Blood 88, 4348-58.

Kumasaka, T., Quinlan, W. M., Doyle, N. A., Condon, T. P., Sligh, J., Takel, F., Beaudet, A., Bennett, C. F., and Doerschuk, C. M. (1996) Role of the intercellular adhesion molecule-1 (ICAM-1) in endotoxin-induced pneumonia evaluated using ICAM-1 antisense oligonucleotides, anti-ICAM-1 monoclonal antibodies, and ICAM-1 mutant mice, J Clin Invest 97, 2362-9.

Kuypers, F. A., Lewis, R. A., Hua, M., Schott, M. A., Discher, D., Ernst, J. D., and Lubin, B. H. (1996). Detection of altered membrane phospholipid asymmetry in subpopulations of human red blood cells using fluorescently labeled annexin V, Blood 87, 1179-87.

Lawler, J., Sunday, M., Thibert, V., Duquette, M., George, E. L., Rayburn, H., and Hynes, R. O. (1998). Thrombospondin-1 is required for normal murine pulmonary homeostasis and its absence causes pneumonia, J Clin Invest 101, 982-92.

Lawrence, M. B., Berg, E. L., Butcher, E. C., and Springer, T. A. (1995). Rolling of lymphocytes and neutrophils on peripheral node addressin and subsequent arrest on ICAM-1 in shear flow, Eur J Immunol 25, 1025-31.

Leder, A., Swan, D., Ruddle, F., D'Eustachio, P., and Leder, P. (1981). Dispersion of alpha-like globin genes of the mouse to three different chromosomes, Nature 293, 196-200.

Lee, S. P., Cunningham, M. L., Hines, P. C., Joneckis, C. C., Orringer, E. P., and Parise, L. V. (1998). Sickle cell adhesion to laminin: potential role for the alpha5 chain, Blood 92, 2951-8.

Ley, K., Bullard, D. C., Arbones, M. L., Bosse, R., Vestweber, D., Tedder, T. F., and Beaudet, A. L. (1995). Sequential contribution of L- and P-selectin to leukocyte rolling in vivo., J Exp Med 181, 669-675.

Mankad, V. N., Williams, J. P., Harpen, M. D., Manci, E., Longenecker, G., Moore, R. B., Shah, A., Yang, Y. M., and Brogdon, B. G. (1990). Magnetic resonance imaging of bone marrow in sickle cell disease: clinical, hematologic, and pathologic correlations, Blood 75, 274-83.

Manodori, A. B., Barabino, G. A., Lubin, B. H., and Kuypers, F. A. (2000). Adherence of phosphatidylserine-exposing erythrocytes to endothelial matrix thrombospondin, Blood 95, 1293-300.

Matsui, N. M., Borsig, L., Rosen, S. D., Yaghmai, M., Varki, A., and Embury, S. H. (2000). The novel adhesion of erythrocytes to P-selectin in sickle cell disease., Blood 96, 600a.

Mazo, I. B., Gutierrez-Ramos, J. C., Frenette, P. S., Hynes, R. O., Wagner, D. D., and von Andrian, U. H. (1998). Hematopoietic progenitor cell rolling in bone marrow microvessels: parallel contributions by endothellal selectins and vascular cell adhesion molecule 1, J Exp Med 188, 465-74.

Metlay, J. P., Witmer-Pack, M. D., Agger, R., Crowley, M. T., Lawless, D., and Steinman, R. M. (1990). The distinct leukocyte integrins of mouse spleen dendritic cells as identified with new hamster monoclonal antibodies, J Exp Med 171, 1753-71.

Mohandas, N., and Evans, E. (1984). Adherence of sickle erythrocytes to vascular endothelial cells: requirement for both cell membrane changes and plasma factors, Blood 64, 282-7.

Mohandas, N., and Evans, E. (1985). Sickle erythrocyte adherence to vascular endothelium. Morphologic correlates and the requirement for divalent cations and collagen-binding plasma proteins, J Clin Invest 76, 1605-12.

Morita, Y., Clemens, M. G., Miller, L. S., Rangen, U., Kondo, S., Miyasaka, M., Yoshikawa, T., and Bulkley, G. B. (1995). Reactive oxidants mediate TNF-alpha-induced leukocyte adhesion to rat mesenteric venular endothelium, Am J Physiol 269, H183342.

Nagel, R. L. (1998). A knockout of a transgenic mouse—animal models of sickle cell anemia, N Engl J Med 339, 194-5.

Nichols, T. C., Samama, C. M., Bellinger, D. A., Roussi, J., Reddick, R. L., Bonneau, M., Read, M. S., Bailliart, G., Koch, G. G., Vaiman, M., and et al. (1995). Function of von Willebrand factor after crossed bone marrow transplantation between normal and von Willebrand disease pigs: effect on arterial thrombosis in chimeras, Proc Natl Acad Sci USA 92,2455-9.

Nishizuka, Y. (1986). Studies and perspectives of protein kinase C, Science 233, 305-12.

Noble, N. A., Xu, Q. P., and Ward, J. H. (1989). Reticulocytes I. Isolation and in vitro maturation of synchronized populations., 74, 475-481.

Noda, H., Kurono, M., Ohishi, N., and Yagi, K. (1993). Stabilization of egg phosphatidylcholine liposomes by the insertion of sulfatide, Biochim Biophys Acta 1153, 127-31.

Papayannopoulou, T., Craddock, C., Nakamoto, B., Priestley, G. V., and Wolf, N. S. (1995). The VLA4/VCAM-1 adhesion pathway defines contrasting mechanisms of lodgement of transplanted murine hemopoletic progenitors between bone marrow and spleen., Proc. Natl Acad Sci USA 92, 9647-9651.

Parsons, S. F., Lee, G., Spring, F. A., Willig, T. N., Peters, L. L., Gimm, J. A., Tanner, M. J., Mohandas, N., Anstee, D. J., and Chasis, J. A. (2001). Lutheran blood group glycoprotein and its newly characterized mouse homologue specifically bind alpha5 chain-containing human laminin with high affinity, Blood 97, 312-20.

Parsons, S. F., Spring, F. A., Chasis, J. A., and Anstee, D. J. (1999). Erythrold cell adhesion molecules Lutheran and LW in health and disease, Baillieres Best Pract Res Clin Haematol 12, 72945.

Paszty, C., Brion, C. M., Manci, E., Witkowska, H. E., Stevens, M. E., Mohandas, N., and Rubin, E. M. (1997). Transgenic knockout mice with exclusively human sickle hemoglobin and sickle cell disease [see comments], Science 278, 876-8.

Pauling, L., Itano, H. A., Singer, S. J., and Wells, I. C. (1949). Sickle cell anemia, a molecular disease., Science 110, 543.

Peled, A., Grabovsky, V., Habler, L., Sandbank, J., Arenzana-Seisdedos, F., Petit, I., Ben-Hur, H., Lapidot, T., and Aion, R. (1999). The chemokine SDF-1 stimulates integrin-mediated arrest of CD34(+) cells on vascular endothelium under shear flow, J Clin Invest 104, 1199-211.

Pemberton, M., Anderson, G., Vetvicka, V., Justus, D. E., and Ross, G. D. (1993). Microvascular effects of complement blockade with soluble recombinant CR1 on ischemia/reperfusion injury of skeletal muscle, J Immunol 150, 5104-13.

Pereira, S., Zhou, M., Mocsai, A., and Lowell, C. (2001). Resting Murine Neutrophils Express Functional alpha (4) Integrins that Signal Through Src Family Kinases, J Immunol 166, 4115-23.

Platt, O. S., Brambilla, D. J., Rosse, W. F., Milner, P. F., Castro, O., Steinberg, M. H., and Klug, P. P. (1994). Mortality in sickle cell disease. Life expectancy and risk factors for early death [see comments], N Engl J Med 330, 1639-44.

Poon, B. Y., Ward, C. A., Cooper, C. B., Giles, W. R., Bums, A. R., and Kubes, P. (2001). alpha(4)-Integrin mediates neutrophil-induced free radical injury to cardiac myocytes, J Cell Biol 152, 857-66.

Ramos, C. L., Huo, Y., Jung, U., Ghosh, S., Manka, D. R., Sarembock, I. J., and Ley, K. (1999). Direct demonstration of P-selectin- and VCAM-1-dependent mononuclear cell rolling in early atherosclerotic lesions of apolipoprotein E-deficient mice, Circ Res 84, 123744.

Ramos, C. L., Kunkel, E. J., Lawrence, M. B., Jung, U., Vestweberi D., Bosse, R., McIntyre, K. W., Gillooly, K. M., Norton, C. R., Wolitzky, B. A., and Ley, K. (1997). Differential effect of E-selectin antibodies on neutrophil rolling and recruitment to inflammatory sites, Blood 89, 3009-18.

Rao, V. M., Mitchell, D. G., Rifkin, M. D., Steiner, R. M., Burk, D. L., Levy, D., and Ballas, S. K. (1989). Marrow infarction in sickle cell anemia: correlation with marrow type and distribution by MRI, Magn Reson Imaging 7, 39-44.

Rhee, P., Morris, J., Durham, R., Hauser, C., Cipolle, M., Wilson, R., Luchette, F., McSwain, N., and Miller, R. (2000). Recombinant humanized monoclonal antibody against CD18 (rhuMAb CD18) in traumatic hemorrhagic shock: results of a phase II clinical trial. Traumatic Shock Group, J Trauma 49, 611-9; discussion 619-20.

Roberts, D. D., Rao, C. N., Liotte, L. A., Gralnick, H. R., and Ginsburg, V. (1986). Comparison of the specificities of laminin, thrombospondin, and von Willebrand factor for binding to sulfated glycolipids, J Biol Chem 261, 6872-7.

Robinson, S. D., Frenette, P. S., Rayburn, H., Cummiskey, M., Ullman-Cullere, M., Wagner, D. D., and Hynes, R. O. (1999). Multiple, targeted deficiencies in selectins reveal a predominant role for P-selectin in leukocyte recruitment, Proc Natl Aced Sci USA 96, 11452-7.

Roszell, N. J., Danton, M. J., Daugherty, C., Overton, A., Grimes, T., girdler, B., Degen, J. L., and Joiner, C. H. (1999). SAD sickle cell disease and fibrinogen deletion: negative interactive effects on mouse survival and organ vasculopathy., blood 94, 198a.

Ryan, T. M., Ciavatta, D. J., and Townes, T. M. (1997). Knockout-transgenic mouse model of sickle cell disease [see comments], Science 278, 873-6.

Saleh, A. W., Hillen, H. F., and Duits, A. J. (1999). Levels of endothelial, neutrophil and platelet-specific factors in sickle cell anemia patients during hydroxyurea therapy, Acta Haematol 102, 31-7.

Sambrano, G. R., and Steinberg, D. (1995). Recognition of oxidatively damaged and apoptotic cells by an oxidized low density lipoprotein receptor on mouse peritoneal macrophages: role of membrane phosphatidylserine, Proc Natl Acad Sci USA 92, 1396-400.

Scharffetter-Kochanek, K., Lu, H., Norman, K., van Nood, N., Munoz, F., Grabbe, S., McArthur, M., Lorenzo, I., Kaplan, S., Ley, K., et al. (1998). Spontaneous skin ulceration and defective T cell function in CD18 null mice, J Exp Med 188, 119-31.

Scheynius, A., Camp, R. L., and Pure, E. (1993). Reduced contact sensitivity reactions in mice treated with monoclonal antibodies to leukocyte function-associated molecule-1 and intercellular adhesion molecule-1, J Immunol 150, 655-63.

Schwartz, R. S., Musto, S., Fabry, M. E., and Nagel, R. L. (1998). Two distinct pathways mediate the formation of intermediate density cells and hyperdense cells from normal density sickle red blood cells, Blood 92, 4844-55.

Schwartz, R. S., Tanaka, Y., Fidler, I. J., Chiu, D. T., Lubin, B., and Schroit, A. J. (1985). Increased adherence of sickled and phosphatidylserine-enriched human erythrocytes to cultured human peripheral blood monocytes, J Clin Invest 75, 1965-72.

Schweitzer, K. M., Drager, A. M., van der Valk, P., Thijsen, S. F. T., Zevenbergen, A., Theijsmeijer, A. P., van der Schoot, C. E., and Lahgenhuijsen, M. M. A. C. (1996). Constitutive expression of E-selectin and vascular cell adhesion molecule-1 on endothelial cells of hematopoietic tissues., Am J Pathol 148, 165-175.

Serqeant, G. R. (1993). The clinical features of sickle cell disease, Baillieres Clin Haematol 6, 93-115.

Shatill, S. J. (1995). Function and regulation of the beta 3 integrins in hemostasis and vascular biology, Thromb Haemost 74, 149-55.

Smyth, S. S., Tsakiris, D. A., Scudder, L. E., and Coller, B. S. (2000). Structure and function of murine alphaIIbbeta3 (GPIIb/IIIa): studies using monoclonal antibodies and beta3-null mice, Thromb Haemost 84, 1103-8.

Southern, E. M. (1988). Prospects for a complete molecular map of the human genome, Philos Trans R Soc Lond B Biol Sci 319, 299-307.

Springer, T. A. (1995). Traffic signals on endothelium for lymphocyte recirculation and leukocyte emigration., Annu Rev Physiol 57, 827-872.

Subramaniam, M., Frenette, P. S., Saffaripour, S., Hynes, R. O., and Wagner, D. D. (1996). Defects in hemoslasis in P-selectin-deficient mice., Blood 87,1238-1242.

Sugihara, K., Sugihara, T., Mohandas, N., and Hebbel, R. P. (1992). Thrombospondin mediates adherence of CD36+ sickle reticulocytes to endothelial cells, Blood 80, 2634-42.

Swerlick, R. A., Eckman, J. R., Kumar, A., Jeitler, M., and Wick, T. M. (1993). Alpha 4 beta 1-integrin expression on sickle reticulocytes: vascular cell adhesion molecule-1-dependent binding to endothelium, Blood.82, 1891-9.

Tait, J. F., and Smith, C. (1999). Phosphatidylserine receptors: role of CD36 in binding of anionic phospholipid vesicles to monocytic cells, J Biol Chem 274, 3048-54.

Takei, F. (1985). Inhibition of mixed lymphocyte response by a rat monoclonal antibody to a novel murine lymphocyte activation antigen (MALA-2), J Immunol 134, 1403-7.

Taooka, Y., Chen, J., Yednock, T., and Sheppard, D. (1999). The integrin alpha9beta1 mediates adhesion to activated endothelial tells and transendothelial neutrophil migration through interaction with vascular cell adhesion molecule-1, J Cell Biol 145, 413-20.

Terpstra, V., and van Berkel, T. J. (2000). Scavenger receptors on liver Kupffer cells mediate the in vivo uptake of oxidatively damaged red blood cells in mice, Blood 95, 2157-63.

Thevenin, B. J. M., Crandall, I., Ballas, S. K., Sherman, I. W., and Shohet, S. B. (1997). Band 3 peptides block the adherence of sickle cells to endothelial cells in vitro, Blood 90, 4172-9.

Trudel, M., De Paepe, M. E., Chretien, N., Saadane, N., Jacmain, J., Sorette, M., Hoang, T., and Beuzard, Y. (1994). Sickle cell disease of transgenic SAD mice, Blood 84, 3189-97.

Trudel, M., Saadane, N., Garel, M. C., Bardakdjlan-Michau, J., Blouquit, Y., Guerquin-Kern, J. L., Rouyer-Fessard, P., Vidaud, D., Pachnis, A., Romeo, P. H., et al. (1991). Towards a transgenic mouse model of sickle cell disease: hemoglobin SAD, Embo J 10, 3157-65.

Udani, M., Zen, Q., Cottman, M., Leonard, N., Jefferson, S., Daymont, C., Truskey, G., and Telen, M. J. (1998). Basal cell adhesion molecule/lutheran protein. The receptor critical for sickle cell adhesion to laminin, J Clin Invest 101, 2550-8.

Vestweber, D., and Blanks, J. E. (1999). Mechanisms that regulate the function of the selectins and their ligands, Physiol Rev 79,181-213.

von Andrian, U. H., Chambers, J. D., McEvoy, L. M., Bargatze, R. F., Arfors, K. E., and Butcher, E. C. (1991). Two-step model of leukocyte-endothelial cell interaction in inflammation: Distict roles for LECAM-1 and the leukocyte B2 integrin in vivo., Proc Natl Acad Sci USA 88, 7538-7542.

Wautier, J. L., Pintigny, D., Wautier, M. P., Paton, R. C., Galacteros, F., Passa, P., and Caen, J. P. (1983). Fibrinogen, a modulator of erythrocyte adhesion to vascular endothelium, J Lab Clin Med 101, 911-20.

Weiss, L. A., Sakal, N, Ghebremariam, B., Ni, C., and Matile, S. (1997). Rigid rod-shaped polyols: functional nonpeptide models for transmembrane proton channels., J Am Chem Soc 119, 12142-12149.

Whitelaw, E., Tsai, S. F., Hogben, P., and Orkin, S. H. (1990). Regulated expression of globin chains and the erythroid transcription factor GATA-1 during erythropoiesis in the developing mouse, Mol Cell Biol 10, 6596-606.

Wick, T. M., Moake, J. L., Udden, M. M., Eskin, S. G. Sears, D. A., and McIntire, L. V. (1987). Unusually large von Willebrand factor multimers increase adhesion of sickle erythrocytes to human endothelial cells under controlled flow, J Clin Invest 80, 905-10.

Wilson, R. W., Ballantyne, C. M., Smith, C. W., Montgomery, C., Bradley. A., O'Brien, W. E., and Beaudet, A. L. (1993). Gene targeting yields a CD-18-mutant mouse for study of inflammation, J Immunol 151, 1571-1578.

Wood, B. L., Gibson, D. F., and Tait, J. F. (1996). Increased erythrocyte phosphatidylserine exposure in sickle cell disease: flow-cytometric measurement and clinical associations, Blood 88, 1873-80.

Xie, X., Raud, J., Hedqvist, P., and Lindbom, L. (1997). In vivo rolling and endothelial selectin binding of mononuclear leukocytes is distinct from that of polymorphonuclear cells, Eur J Immunol 27, 2935-41.

Various publications are cited herein, the contents of which are hereby incorporated by reference in their entireties.

What is claimed is:

1. A method of treating a sickle cell disease subject in vaso-occlusive crisis comprising administering an E-selectin inhibitor that interacts with a calcium-binding lectin domain of E-selectin in an amount effective to treat the subject.

* * * * *